(12) United States Patent
Fischetti et al.

(10) Patent No.: US 8,105,585 B2
(45) Date of Patent: Jan. 31, 2012

(54) PLY-GBS MUTANT LYSINS

(75) Inventors: Vincent A. Fischetti, West Hempstead, NY (US); Qi Cheng, Morrisville, NC (US)

(73) Assignee: The Rockefeller Universtiy, New York, NY (US)

( * ) Notice: Subject to any disclaimer, the term of this patent is extended or adjusted under 35 U.S.C. 154(b) by 691 days.

(21) Appl. No.: 12/064,428

(22) PCT Filed: Aug. 17, 2006

(86) PCT No.: PCT/US2006/032176
§ 371 (c)(1),
(2), (4) Date: Apr. 1, 2008

(87) PCT Pub. No.: WO2007/024628
PCT Pub. Date: Mar. 1, 2007

(65) Prior Publication Data
US 2008/0221035 A1 Sep. 11, 2008

Related U.S. Application Data

(60) Provisional application No. 60/710,936, filed on Aug. 24, 2005.

(51) Int. Cl.
*A61K 38/43* (2006.01)
*A61K 38/48* (2006.01)

(52) U.S. Cl. .................................. 424/94.6; 424/94.63

(58) Field of Classification Search ............... 424/94.63, 424/93.6
See application file for complete search history.

(56) References Cited

U.S. PATENT DOCUMENTS

| | | | | |
|---|---|---|---|---|
| 4,179,337 A | 12/1979 | Davis et al. | ............... | 435/181 |
| 4,301,144 A | 11/1981 | Iwashita et al. | ............... | 424/78 |
| 4,496,689 A | 1/1985 | Mitra | ............... | 525/54.1 |
| 4,615,697 A | 10/1986 | Robinson | ............... | 604/890 |
| 4,640,835 A | 2/1987 | Shimizu et al. | ............... | 424/94 |
| 4,670,417 A | 6/1987 | Iwasaki et al. | ............... | 514/6 |
| 4,680,338 A | 7/1987 | Sundoro | ............... | 525/54.1 |
| 4,791,192 A | 12/1988 | Nakagawa et al. | ............... | 530/399 |
| 4,948,580 A | 8/1990 | Browning | ............... | 424/78 |
| 5,413,792 A | 5/1995 | Ninomiya et al. | ............... | 424/434 |
| 5,428,130 A | 6/1995 | Capon et al. | ............... | 530/350 |
| 5,554,380 A | 9/1996 | Cuca et al. | ............... | 424/441 |
| 5,654,010 A | 8/1997 | Johnson et al. | ............... | 424/502 |
| 5,808,022 A | 9/1998 | Huse | ............... | 536/22.1 |
| 5,863,560 A | 1/1999 | Osborne | ............... | 424/484 |
| 5,942,243 A | 8/1999 | Shah | ............... | 424/434 |
| 5,976,862 A | 11/1999 | Kauffman et al. | ............... | 435/252.3 |
| 6,056,954 A | 5/2000 | Fischetti et al. | ............... | 424/94.1 |
| 6,056,955 A | 5/2000 | Fischetti et al. | ............... | 424/94.1 |
| 6,132,970 A | 10/2000 | Stemmer | ............... | 435/6 |
| 7,402,309 B2 | 7/2008 | Fischetti et al. | | |
| 7,569,223 B2 | 8/2009 | Fischetti et al. | | |
| 7,582,291 B2 | 9/2009 | Yoong et al. | | |
| 7,638,600 B2 | 12/2009 | Fischetti et al. | | |
| 2005/0004030 A1 | 1/2005 | Fischetti et al. | | |

FOREIGN PATENT DOCUMENTS

| | | |
|---|---|---|
| WO | WO 87/05330 A1 | 9/1987 |
| WO | WO 96/07399 A1 | 3/1996 |
| WO | WO 96/40072 A2 | 12/1996 |
| WO | WO 97/03692 A1 | 2/1997 |
| WO | WO 2007/024628 A2 | 1/2007 |
| WO | WO 2007/024628 A3 | 1/2007 |
| WO | WO2010002959 | 1/2010 |

OTHER PUBLICATIONS

Pritchard et al. Microbiology, Jul. 2004, vol. 150, pp. 2079-2087.*
Altschul, Stephen F., et al., "Gapped BLAST and PSI-BLAST: a new generation of protein database search programs," Nucleic Acids Res., 1997, vol. 25, No. 17, pp. 3389-3402.
Aplin, John D., et al., "Preparation, Properties, and Applications of Carbohydrate Conjugates of Proteins and Lipids," CRC Crit. Rev. Biochem., 1981, pp. 259-306.
Ausubel, Frederick M., et al., "Short Protocols in Molecular Biology, Second Edition—A Compendium of Methods from Current Protocols in Molecular Biology," 1992, Green Publishing Associates and John Wiley & Sons, pp. iii-xviii and 16-33-16-48.
Bolton, E.T., et al., "A General Method for the Isolation of RNA Complementary to DNA," Biochemistry: Bolton and McCarthy, Proc. N. A. S., USA, 1962, vol. 48, pp. 1390-1397.
Bonner Tom I., et al., "Reduction in the Rate of DNA Reassociation by Sequence Divergence," J. Mol. Biol., 1973, vol. 81, pp. 123-135.
Church, George M., et al., "Genomic sequencing," Proc. Natl. Acad. Sci. USA, 1984 vol. 81, pp. 1991-1995.
Cheng, Q., et al., "Removal of group B streptococci colonizing the vagina and oropharynx of mice with a bacteriophage lytic enzyme," Antimicrob. Agents Chemother., 2005, vol. 49, pp. 111-117.
Cleland, Jeffrey L., "Design and Production of Single-Immunization Vaccines Using Polylactide Polyglycolide Microsphere Systems," Vaccine Design: The Subunit and Adjuvant Approach, Powell and Newman, eds, Plenum Press: New York, 1995, pp. 439-462.
Cotton, Richard G. H., et al., "Reactivity of cytosine and thymine in single-base-pair mismatches with hydroxylamine and osmium tetroxide and its application to the study of mutations," Proc. Natl. Acad. Sci. USA, 1988, vol. 85, pp. 4397-4401.
Delagrave, Simon, et al., "Recursive ensemble mutagenesis," Protein Engineering, 1993, vol. 6, No. 3, pp. 327-331.
Gebeyehu, Gulilat, et al., "Novel bioinylated nucleotide—analogs for labeling and colorimetric detection of DNA," Nucleic Acids Research, 1987, vol. 15, No. 11, pp. 4513-4534, IRL Press Limited, Oxford, England.
Hora, Maninder Singh, et al., "Controlled Release of Interleukin-2 from Biodegradable Microspheres," Bio/Technology, 1990, vol. 8, pp. 755-758, Nature Publishing Group.
Ike, Yoshimasa, et al., "Solid phase synthesis of polynucleotides. VIII. Synthesis of mixed oligodeoxyribonucleotides by the phosphotriester solid phase method[1]," Nucleic Acids Research, 1983, vol. 11, No. 2, pp. 477-488.
Itakura, K., et al., Synthesis and Use of Synthetic Oligonucleotides, Ann. Rev. Biochem., 1984, vol. 53, pp. 323-356.

(Continued)

*Primary Examiner* — Tekchand Saidha
(74) *Attorney, Agent, or Firm* — Klauber & Jackson LLC

(57) ABSTRACT

Methods, compositions and articles of manufacture useful for the treatment of various Group B streptococci (GBS) bacteria using various lysins, including certain PlyGBS mutant lysins, are provided.

18 Claims, 9 Drawing Sheets

OTHER PUBLICATIONS

Johnson, Oufunmi L., et al., "A month-long effect from a single injection of microencapsulated human growth hormone," Nature Medicine, 1996, vol. 2, No. 7, pp. 795-799, Nature Publishing Group.

Loeffler, J.M., et al., "Rapid Killing of Streptococcus pneumoniae with a Bacteriophage Cell Wall Hydrolase," Science, 2001, vol. 294, pp. 2170-2172.

Loessner, Martin J., et al., "Evidence for a Holin-Like Protein Gene Full Embedded Out of Frame in the Endolysin Gene of Staphylococcus aureus Bacteriophage 187," Journal of Bacteriology, 1999, vol. 181, No. 15, pp. 4452-4460.

Loessner, Martin J., et al., "Three Bacillus cereus Bacteriophage Endolysins are Unrelated but Review High Homology to Cell Well Hydrolases from Different Bacilli," Journal of Bacteriology, 1997, vol. 179, No. 9, pp. 2845-2851.

Loessner, Martin J., et al., "Heterogeneous endolysins in Listeria monocytogenes bacteriophages: a new class of enzymes and evidence for conserved holing genes within the siphoviral lysis cassettes," Molecular Microbiology, 1995, vol. 16, No. 6, pp. 1231-1241.

Lopez, R., et al., "The pneumococcal cell wall degrading enzymes: a modular design to create new lysins?," Microbial Drug Resistance, 1997, vol. 3, No. 2, pp. 199-211.

Lopez, R., et al., "Biological roles of two murein hydrolases of Streptococcus pneumoniae representing examples of module shuffling," Res. Microbiol. 2000, vol. 151, pp. 437-443.

Myers, R., et al., "Detection of Single Base Substitutions by Ribonuclease Cleavage at Mismatches in RNA:DNA Duplexes," Science, 1985, vol. 230, pp. 1242-1246.

Myers, R.M., et al., "Recent Advances in the Development of Methods for Detecting Single-base Substitutions Associated with Human Genetic Diseases," Cold Spring Harbor Symposium on Quantitative Biology, 1986, vol. 51, pp. 275-284.

Narang, Saran A., "Tetrahedron Report No. 140 DNA Synthesis," Tetrahedra, 1983, vol. 39, No. 1, pp. 3-22.

Nelson, D., et al., "Prevention and elimination of upper respiratory colonization of mice by group A streptococci by using a bacteriophage lytic enzyme," Prot. Natl. Acad. Sci. USA, 2001, vol. 98, No. 7, 4107-4112.

Pritchard, D.G., et al., "The bifunctional peptidoglycan lysin of Streptococcus agalactiae bacteriophage B30," Microbiology, 2004, vol. 150, pp. 2079-2087.

Sambrook, J., et al., "Molecular Cloning: A Laboratory Manual, $2^{nd}$ Ed.", Cold Spring Harbor Laboratory Press, Cold Spring Harbor, New York (1989).

Southern, E.M., "Detection of Specific Sequences Among DNA Fragments Separated by Gel Electrophoresis," J. Mol. Biol., 1975, vol. 98, pp. 503-517.

Stoflet, E.S., et al., "Genomic Amplification with Transcript Sequencing," Science, 1988, vol. 239, pp. 491-494.

Wallace, R.B., et al., "Application of Synthetic DNA Probes to the Analysis of DNA Sequence Variants in Man," Cold Harbor Spring Symposium on Quantitative Biology, 1986, vol. 51, pp. 257-261.

Young, R., et al., "Phages will out: strategies of host cell lysis," Trends in Microbiology, 2000, vol. 8, No. 3, pp. 120-128.

Reinscheid, D.J., et al., "Identification and Molecular Analysis of PcsB, a Protein Required for Cell Wall Separation of Group B Streptococcus," Journal of Bacteriology, Feb. 2001, pp. 1175-1183.

* cited by examiner

Fig. 1

| SEQ ID NO: | Description | Sequence |
|---|---|---|
| 1 | PlyGBS | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN AVTVTDNTGL NKGDYFIDVS AYQQADLTTT CQQAGTTKTI IKVSESIAWL SDRHQQQANT SDPIGYYHFG RFGGDSALAQ READLFLSNL PSKKVSYLVI DYEDSASADK QANTNAVIAF MDKIASAGYK PIYYSYKPFT LNNIDYQKII AKYPNSIWIA GYPDYEVRTE PLWEFFPSMD GVRWWQFTSV GVAGGLDKNI VLLADDSSKM DIPKVDKPQE LTFYQKLATN TKLENSNVPY YEATLSTDYY VESKPNASSA DKEFIKAGTR VRVYEKVNGW SRINHPESAQ WVEDNYLVNA TDM |
| 2 | PlyGBS 86-6 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN AVTVTDNTGL NKGDYFIDVS AYQQADLTTT CQQAGTTKTI IKVSESIAWL SDRHQQQANT SDPIGYYHFG RFGGDSALAQ READLFLSNL PSKKVSYLVI DYEDSASADK QANTNAVIAF MDKIASAGYK PIYYSYKPFT LNNIDYQKII AKYPNSIWIA GYPDYEVRTE PLWEFFPSMD GVRWWQFTSV GVAGGLDKNI VLLADDSSKM DIPKVDKPQE LTFYQKLATN TKLENSNVPY YEATLSTDYY VESKPNASSA DKEFIKAGTR VRVYEKVNGW SRINHPESAQ WVEDNYLVNA TDM |
| 3 | PlyGBS 80 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN AVTVTDNTGL NKGDYFIDVS AYQ |
| 4 | PlyGBS 90-8 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSF |
| 5 | PlyGBS 90-1 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN ADGHALTIQS RRNG |
| 6 | PlyGBS 92 mutant | L NKGDYFIDVS AYQQADLTTT CQQAGTTKTI IKVSESIAWL SDRHQQQANT SDPIGYYHFG RFGGDSALAQ READLFLSNL PSKKVSYLVI DYEDSASADK QANTNAVIAF MDKIASAGYK PIYYSYKPFT LNNIDYQKII AKYPNSIWIA GYPDYEVRTE PLWEFFPSMD GVRWWQFTSV GVAGGLDKNI VLLADDSSKM DIPKVDKPQE LTFYQKLATN TKLDNSNVPY YEATLSTDYY VESK |
| 7 | PlyGBS 93 mutant | L NKGDYFIDVS AYQQADLTTT CQQAGTTKTI IKVSESIAWL SDRHQQQANT SDPIGYYHFG RFGGDSALAQ READLFLSNL PSKKVSYLVI DYEDSASADK QANTNAVIAF MDKIASAGYK PIYYSYKPFT LNNIDYQKII AKYPNSIWIA GYPDYEVRTE PLWEFFPSMD GVRWWQFTSV GVAGGLDKNI VLLADDSSKM DIPKVDKPQE LTFYQKLATN TKLDNSNVPY YEATLSTDYY VESKPNASSA DKEFIKAGTR VRVYEKVNGW SRINHPESAQ WVEDNYLVNA TDM |
| 8 | PlyGBS 94 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN AVTVTD |
| 9 | PlyGBS 95 mutant | MATYQEYKSR SNGNAYDIDG SFGAQCWDGY ADYCKYLGLP YANCTNTGYA RDIWEQRHEN GILNYFDEVE VMQAGDVAIF MVVDGVTPYS HVAIFDSDAG GGYGWFLGQN QGGANGAYNL VKIPYSATYP TAFRPKSFKN AVTVTD KM DIPKVDKPQE LTFYQKLATN TKLDNSNVPY YEATLSTDYY VESKPNASSA DKEFIKAGTR VRVYEKVNGW SRINHPESAQ WVEDNYLVNA TDM |

Fig. 4

| | | endopeptidase | muramidase | Activity |
|---|---|---|---|---|
| SEQ ID NO:1 | PlyGBS | 1  107 | 150  394  443 | 1 |
| SEQ ID NO:6 | PlyGBS92 | | 150  394 | ND |
| SEQ ID NO:7 | PlyGBS93 | | 150  443 | ND |
| SEQ ID NO:8 | PlyGBS94 | 1  146 | | ~25 fold |
| SEQ ID NO:9 | PlyGBS95 | 1  146 | 349  443 | ~25 fold |

Fig. 5
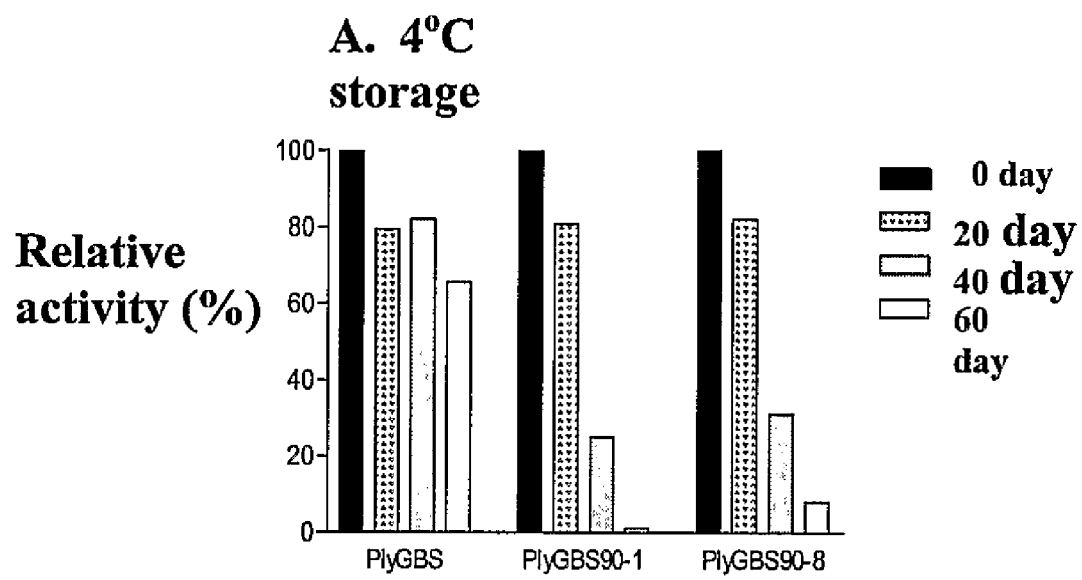
A. 4°C storage
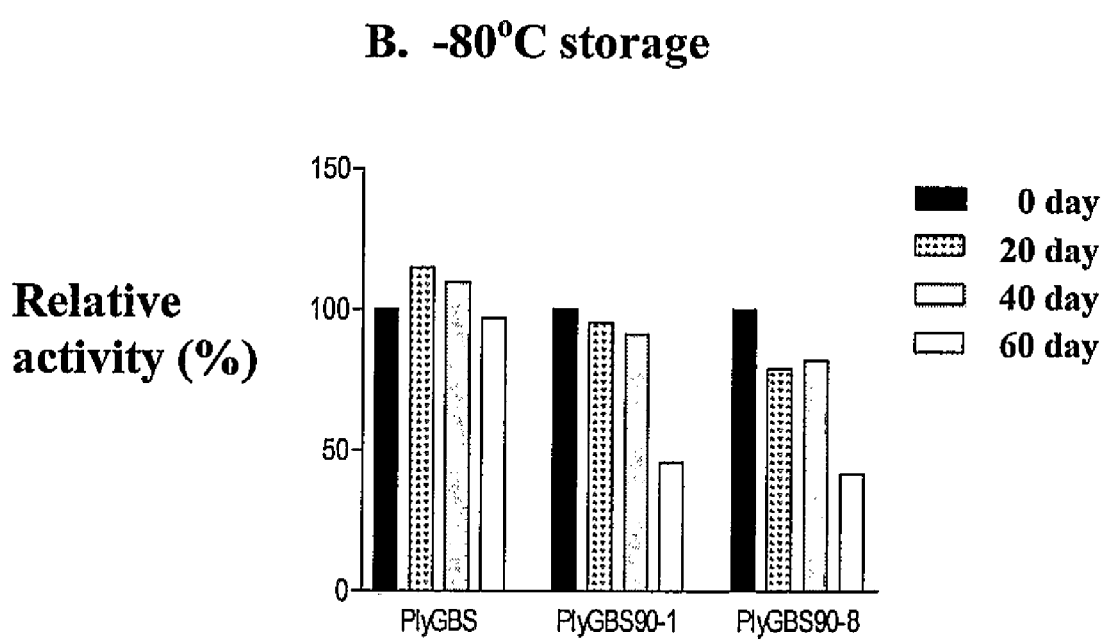
B. -80°C storage

Fig. 6
A.
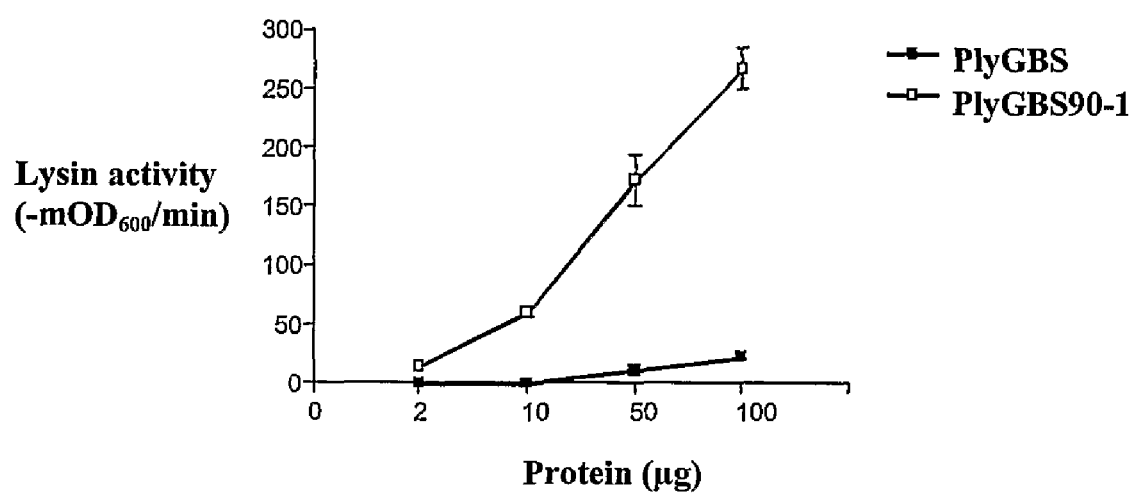
B.
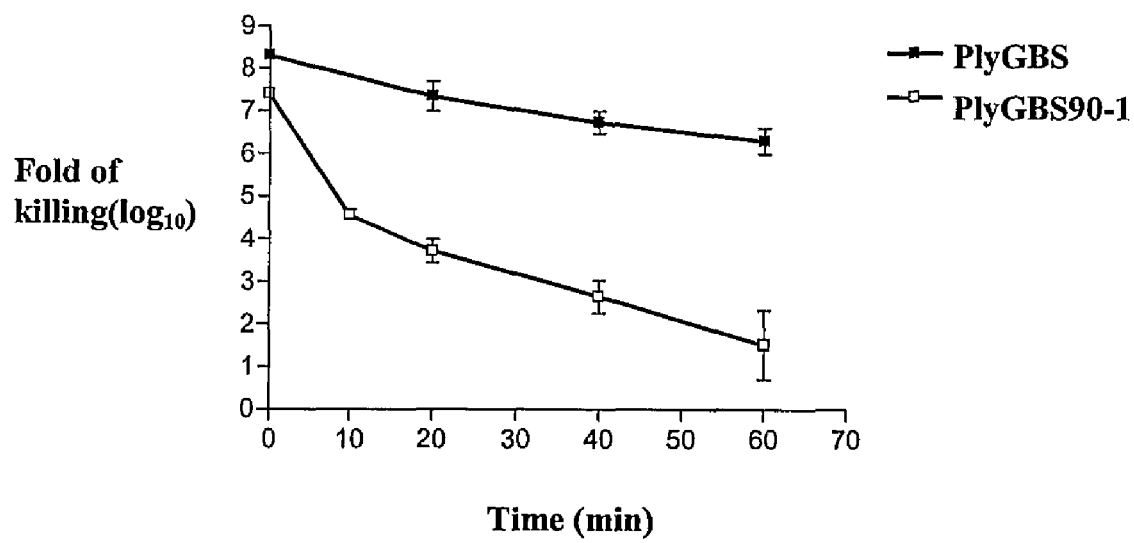

```
                        SEQUENCE LISTING

<160> NUMBER OF SEQ ID NOS: 9

<210> SEQ ID NO 1
<211> LENGTH: 443
<212> TYPE: PRT
<213> ORGANISM: Streptococcus agalactiae

<400> SEQUENCE: 1

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe Lys Asn Ala Val Thr Val
    130                 135                 140
```

```
Thr Asp Asn Thr Gly Leu Asn Lys Gly Asp Tyr Phe Ile Asp Val Ser
145                 150                 155                 160

Ala Tyr Gln Gln Ala Asp Leu Thr Thr Thr Cys Gln Gln Ala Gly Thr
                165                 170                 175

Thr Lys Thr Ile Ile Lys Val Ser Glu Ser Ile Ala Trp Leu Ser Asp
            180                 185                 190

Arg His Gln Gln Gln Ala Asn Thr Ser Asp Pro Ile Gly Tyr Tyr His
        195                 200                 205

Phe Gly Arg Phe Gly Gly Asp Ser Ala Leu Ala Gln Arg Glu Ala Asp
    210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
            260                 265                 270

Tyr Tyr Ser Tyr Lys Pro Phe Thr Leu Asn Asn Ile Asp Tyr Gln Lys
        275                 280                 285

Ile Ile Ala Lys Tyr Pro Asn Ser Ile Trp Ile Ala Gly Tyr Pro Asp
    290                 295                 300

Tyr Glu Val Arg Thr Glu Pro Leu Trp Glu Phe Phe Pro Ser Met Asp
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Ser Ser Lys Met Asp Ile
            340                 345                 350

Pro Lys Val Asp Lys Pro Gln Glu Leu Thr Phe Tyr Gln Lys Leu Ala
        355                 360                 365

Thr Asn Thr Lys Leu Asp Asn Ser Asn Val Pro Tyr Tyr Glu Ala Thr
    370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Tyr Glu Lys
                405                 410                 415

Val Asn Gly Trp Ser Arg Ile Asn His Pro Glu Ser Ala Gln Trp Val
            420                 425                 430

Glu Asp Asn Tyr Leu Val Asn Ala Thr Asp Met
        435                 440

<210> SEQ ID NO 2
<211> LENGTH: 443
<212> TYPE: PRT
<213> ORGANISM: Artificial Sequence
<220> FEATURE:
<223> OTHER INFORMATION: Modified Streptococcus agalactiae sequence

<400> SEQUENCE: 2

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
                20                  25                  30

Tyr Cys Lys Tyr Leu Gly Leu Pro Tyr Ala Asn Cys Thr Asn Thr Gly
            35                  40                  45

Tyr Ala Arg Asp Ile Trp Glu Gln Arg His Glu Asn Gly Ile Leu Asn
        50                  55                  60

Tyr Phe Asp Glu Val Glu Val Met Gln Ala Gly Asp Val Ala Ile Phe
```

```
            65                  70                  75                  80
Met Val Val Asp Gly Val Thr Pro Tyr Ser His Val Ala Ile Phe Asp
                    85                  90                  95

Ser Asp Ala Gly Gly Tyr Gly Trp Phe Leu Gly Gln Asn Gln Gly
                100                 105                 110

Gly Ala Asn Gly Ala Tyr Asn Leu Val Lys Ile Pro Tyr Ser Ala Thr
                115                 120                 125

Tyr Pro Thr Ala Phe Arg Pro Lys Ser Phe Lys Asn Ala Val Thr Val
                130                 135                 140

Thr Asp Asn Thr Gly Leu Asn Lys Gly Asp Tyr Phe Ile Asp Val Ser
145                 150                 155                 160

Ala Tyr Gln Gln Ala Asp Leu Thr Thr Thr Cys Gln Gln Ala Gly Thr
                165                 170                 175

Thr Lys Thr Ile Ile Lys Val Ser Glu Ser Ile Ala Trp Leu Ser Asp
                180                 185                 190

Arg His Gln Gln Gln Ala Asn Thr Ser Asp Pro Ile Gly Tyr Tyr His
                195                 200                 205

Phe Gly Arg Phe Gly Gly Asp Ser Ala Leu Ala Gln Arg Glu Ala Asp
                210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
                260                 265                 270

Tyr Tyr Ser Tyr Lys Pro Phe Thr Leu Asn Asn Ile Asp Tyr Gln Lys
                275                 280                 285

Ile Ile Ala Lys Tyr Pro Asn Ser Ile Trp Ile Ala Gly Tyr Pro Asp
                290                 295                 300

Tyr Glu Val Arg Thr Glu Pro Leu Trp Glu Phe Phe Pro Ser Met Asp
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Asp Ser Ser Lys Met Asp Ile
                340                 345                 350

Pro Lys Val Asp Lys Pro Gln Glu Leu Thr Phe Tyr Gln Lys Leu Ala
                355                 360                 365

Thr Asn Thr Lys Leu Glu Asn Ser Asn Val Pro Tyr Tyr Glu Ala Thr
                370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Val Tyr Glu Lys
                405                 410                 415

Val Asn Gly Trp Ser Arg Ile Asn His Pro Glu Ser Ala Gln Trp Val
                420                 425                 430

Glu Asp Asn Tyr Leu Val Asn Ala Thr Asp Met
                435                 440
```

<210> SEQ ID NO 3
<211> LENGTH: 163
<212> TYPE: PRT
<213> ORGANISM: Artificial Sequence
<220> FEATURE:
<223> OTHER INFORMATION: Modified Streptococcus agalactiae sequence

<400> SEQUENCE: 3

-continued

```
Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe Lys Asn Ala Val Thr Val
    130                 135                 140

Thr Asp Asn Thr Gly Leu Asn Lys Gly Asp Tyr Phe Ile Asp Val Ser
145                 150                 155                 160

Ala Tyr Gln

<210> SEQ ID NO 4
<211> LENGTH: 138
<212> TYPE: PRT
<213> ORGANISM: Artificial Sequence
<220> FEATURE:
<223> OTHER INFORMATION: Modified Streptococcus agalactiae sequence

<400> SEQUENCE: 4

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe
    130                 135

<210> SEQ ID NO 5
<211> LENGTH: 154
<212> TYPE: PRT
<213> ORGANISM: Artificial Sequence
<220> FEATURE:
<223> OTHER INFORMATION: Modified Streptococcus agalactiae sequence

<400> SEQUENCE: 5
```

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
            85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
            115                 120                 125

Tyr Pro Thr Ala Phe Arg Pro Lys Ser Phe Lys Asn Ala Asp Gly His
    130                 135                 140

Ala Leu Thr Ile Gln Ser Arg Arg Asn Gly
145                 150

<210> SEQ ID NO 6
<211> LENGTH: 245
<212> TYPE: PRT
<213> ORGANISM: Artificial Sequence
<220> FEATURE:
<223> OTHER INFORMATION: Modified Streptococcus agalactiae

<400> SEQUENCE: 6

Leu Asn Lys Gly Asp Tyr Phe Ile Asp Val Ser Ala Tyr Gln Gln Ala
1               5                   10                  15

Asp Leu Thr Thr Thr Cys Gln Gln Ala Gly Thr Thr Lys Thr Ile Ile
            20                  25                  30

Lys Val Ser Glu Ser Ile Ala Trp Leu Ser Asp Arg His Gln Gln Gln
        35                  40                  45

Ala As

```
                    210                 215                 220

Asp Asn Ser Asn Val Pro Tyr Tyr Glu Ala Thr Leu Ser Thr Asp Tyr
225                 230                 235                 240

Tyr Val Glu Ser Lys
                245

<210> SEQ ID NO 7
<211> LENGTH: 294
<212> TYPE: PRT
<213> ORGANISM: Artificial Sequence
<220> FEATURE:
<223> OTHER INFORMATION: Modified Streptococcus agalactiae sequence

<400> SEQUENCE: 7

Leu Asn Lys Gly Asp Tyr Phe Ile Asp Val Ser Ala Tyr Gln Gln Ala
1               5                   10                  15

Asp Leu Thr Thr Thr Cys Gln Gln Ala Gly Thr Thr Lys Thr Ile Ile
                20                  25                  30

Lys Val Ser Glu Ser Ile Ala Trp Leu Ser Asp Arg His Gln Gln Gln
            35                  40                  45

Ala Asn Thr Ser Asp Pro Ile Gly Tyr Tyr His Phe Gly Arg Phe Gly
    50                  55                  60

Gly Asp Ser Ala Leu Ala Gln Arg Glu Ala Asp Leu Phe Leu Ser Asn
65                  70                  75                  80

Leu Pro Ser Lys Lys Val Ser Tyr Leu Val Ile Asp Tyr Glu Asp Ser
                85                  90                  95

Ala Ser Ala Asp Lys Gln Ala Asn Thr Asn Ala Val Ile Ala Phe Met
            100                 105                 110

Asp Lys Ile Ala Ser Ala Gly Tyr Lys Pro Ile Tyr Tyr Ser Tyr Lys
        115                 120                 125

Pro Phe Thr Leu Asn Asn Ile Asp Tyr Gln Lys Ile Ile Ala Lys Tyr
    130                 135                 140

Pro Asn Ser Ile Trp Ile Ala Gly Tyr Pro Asp Tyr Glu Val Arg Thr
145                 150                 155                 160

Glu Pro Leu Trp Glu Phe Phe Pro Ser Met Asp Gly Val Arg Trp Trp
                165                 170                 175

Gln Phe Thr Ser Val Gly Val Ala Gly Gly Leu Asp Lys Asn Ile Val
            180                 185                 190

Leu Leu Ala Asp Asp Ser Ser Lys Met Asp Ile Pro Lys Val Asp Lys
        195                 200                 205

Pro Gln Glu Leu Thr Phe Tyr Gln Lys Leu Ala Thr Asn Thr Lys Leu
    210                 215                 220

Asp Asn Ser Asn Val Pro Tyr Tyr Glu Ala Thr Leu Ser Thr Asp Tyr
225                 230                 235                 240

Tyr Val Glu Ser Lys Pro Asn Ala Ser Ser Ala Asp Lys Glu Phe Ile
                245                 250                 255

Lys Ala Gly Thr Arg Val Arg Val Tyr Glu Lys Val Asn Gly Trp Ser
            260                 265                 270

Arg Ile Asn His Pro Glu Ser Ala Gln Trp Val Glu Asp Asn Tyr Leu
        275                 280                 285

Val Asn Ala Thr Asp Met
        290

<210> SEQ ID NO 8
<211> LENGTH: 146
<212> TYPE: PRT
<213> ORGANISM: Artificial Sequence
```

<220> FEATURE:
<223> OTHER INFORMATION: Modified Streptococcus agalactiae sequence

<400> SEQUENCE: 8

```
Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe Lys Asn Ala Val Thr Val
    130                 135                 140

Thr Asp
145
```

<210> SEQ ID NO 9
<211> LENGTH: 241
<212> TYPE: PRT
<213> ORGANISM: Artificial Sequence
<220> FEATURE:
<223> OTHER INFORMATION: Modified Streptococcus agalactiae sequence

<400> SEQUENCE: 9

```
Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe Lys Asn Ala Val Thr Val
    130                 135                 140

Thr Asp Lys Met Asp Ile Pro Lys Val Asp Lys Pro Gln Glu Leu Thr
145                 150                 155                 160

Phe Tyr Gln Lys Leu Ala Thr Asn Thr Lys Leu Asp Asn Ser Asn Val
                165                 170                 175

Pro Tyr Tyr Glu Ala Thr Leu Ser Thr Asp Tyr Tyr Val Glu Ser Lys
            180                 185                 190
```

```
Pro Asn Ala Ser Ser Ala Asp Lys Glu Phe Ile Lys Ala Gly Thr Arg
        195                 200                 205

Val Arg Val Tyr Glu Lys Val Asn Gly Trp Ser Arg Ile Asn His Pro
    210                 215                 220

Glu Ser Ala Gln Trp Val Glu Asp Asn Tyr Leu Val Asn Ala Thr Asp
225                 230                 235                 240

Met
```

PLY-GBS MUTANT LYSINS

CROSS REFERENCE TO RELATED APPLICATIONS

This application is the national phase under 35 U.S.C. §371 of PCT International Application No. PCT/US2006/032176, which has an International filing date of Aug. 17, 2006, which designated the United States of America and is incorporated herein by reference in its entirety, and which in turn claims the benefit of U.S. Provisional Patent Application Ser. No. 60/710,936 entitled PLY-GBS MUTANT LYSINS, filed Aug. 24, 2005, the entire contents of both applications are incorporated herein by reference.

This invention relates to the identification and use of phage associated lytic enzymes to rapidly and specifically detect or kill certain bacteria, such as Group B streptococci (GBS) bacteria.

BACKGROUND

Group B streptococci (GBS), or *Streptococcus agalactiae*, are a major cause of neonatal bacterial infection in the United States (Baker, C. J., and M. S. Edwards, "Group B streptococcal infections," p. 1091-1156 in J. Remmington and J. O. Klein (ed.), *Infectious diseases of the fetus and newborn infants*, 5th ed. The W. B. Saunders Co. Philadelphia, Pa. (2001)). GBS are normally colonized in human genital and lower gastrointestinal tracts and can be vertically transmitted from mother to baby during a normal vaginal delivery. Common manifestations of GBS disease in neonates include sepsis, meningitis, pneumonia and joint infections. About 21% of pregnant women are vaginally colonized with GBS and a significant high percentage of babies develop symptoms associated with GBS infection. For example, sepsis occurs in 16 of 1,000 live births to women with GBS colonization, while only in 0.4 of 1,000 live births to women without GBS colonization (Regan, J. A., M. A. Klebanoff, R. P. Nugent & 7 other authors. 1996. Colonization with group B streptococci in pregnancy and adverse outcome. Am. J. Obstet. Gynecol. 174: 1354-1360).

Intrapartum antibiotic prophylaxis (IAP) is the primary prevention suggested by the Centers for Disease Control and Prevention (CDC) because it can effectively reduce neonatal GBS colonization and early-onset infection (Centers for Disease Control and Prevention, "Prevention of perinatal group B streptococcal disease: a public health perspective," *Morbid. Mortal. Weekly Rep.* 45: 1-24 (1996); and Centers for Disease Control and Prevention, "Prevention of perinatal group B streptococcal disease: revised guidelines from CDC," *Morbid. Mortal. Weekly Rep.* 51: 1-22 (2002)). IAP is usually given to pregnant women colonized with GBS 4 hrs before delivery to prevent vertical transmission. However, there are many places in the world that GBS culture screening is not routine for pregnant women and universal administration of antibiotics may present a potential threat to neonates. Antibiotic resistance is another major concern because some GBS clinical isolates are already found to be resistant to erythromycin and clindamycin (Fernandez, M., M. Hickman, and C. J. Baker, "Antimicrobial susceptibilities of group B streptococci isolated between 1992 and 1996 from patients with bacteremia or meningitis," *Antimicrob. Agents Chemother.* 42: 1517-1519 (1998); Centers for Disease Control and Prevention, "Prevention of perinatal group B streptococcal disease: revised guidelines from CDC", *Morbid. Mortal. Weekly Rep.* 51: 1-22 (2002)). Thus, there is a need for a direct and effective alternative to IAP.

One promising approach to the detection and treatment of pathogenic bacteria is the use of bacteriophage lytic enzymes as bacteriolytic agents. Bacteriophage lytic enzymes responsible for bacterial host lysis are also known as lysins. Many lysins can rapidly break down the bacterial cell wall in order to release progeny phage (Young, R. 1992. Bacteriophage lysis: mechanism and regulation. Microbiol. Rev. 56:430-481). Structurally, lysins are commonly found as modular proteins with an amino terminal domain that confers the enzymatic activity for a peptidoglycan bond and a carboxy terminal domain that confers binding specificity to a carbohydrate epitope in the bacterial cell wall (Loessner, M., K. Kramer, F. Ebel, and S. Scherer, "C-terminal domains of *Listeria monocytogenes* bacteriophage murein hydrolases determine specific recognition and high-affinity binding to bacterial cell wall carbohydrates," (Mol. Microbiol. 44:335-349 (2002); Lopez, R., E. Garcia, P. Garcia, and J. L. Garcia, "The pneumococcal cell wall degrading enzymes: a modular design to create new lysins?," MicroB. Drug Resist. 3:199-211 (1997); Lopez, R., M. P. Gonzalez, E. Garcia, J. L. Garcia, and P. Garcia, "Biological roles of two new murein hydrolases of *Streptococcus pneumoniae* representing examples of module shuffling," Res. Microbiol. 151:437-443 (2002); Sheehan, M. M., J. L. Garcia, R. Lopez, and P. Garcia, "The lytic enzyme of the pnemococcal phage Dp-1: a chimeric enzyme of intergeneric origin," Mol. Microbiol. 25:717-725 (1997)). Lysins are believed to provide at least one of the following enzymatic activities against a peptidoglycan substrate: muramidases, glucosaminidases, N-acetylmuramyl-L-alanine amidase and endopeptidases (Young, R., "Bacteriophage lysis: mechanism and regulation," Microbiol. Rev. 56:430-481 (1992)). Purified lysin from a bacteriophage can be applied exogenously to affect bacterial lysis (Loeffler, J. M., D. Nelson, and V. A. Fischetti, "Rapid killing of *Streptococcus pneumoniae* with a bacteriophage cell wall hydrolase," Science. 294:2170-2172 (2001); Loessner, M., G. Wendlinger, and S. Scherer, "Heterogeneous endolysins in *Listeria monocytogenes* bacteriophages: a new class of enzymes and evidence for conserved holin genes within the siphoviral lysis cassettes," Mol. Microbiol. 16:1231-1241 (1995); Loessner, M., S. K. Maier, H. Daubek-Puza, G. Wendlinger, and S. Scherer, "Three *Bacillus cereus* bacteriophage endolysins are unrelated but reveal high homology to cell wall hydrolases from different *bacilli*," J. Bacteriol. 179:2845-2851 (1997); Nelson, D., L. Loomis, and V. A. Fischetti, "Prevention and elimination of upper respiratory colonization of mice by group A streptococci by using a bacteriophage lytic enzyme," Prot. Natl. Acad. Sci. USA. 98:4107-4112 (2001)).

Lysins are normally very specific to the bacterial species from which the lysin derived phage was isolated (Fischetti, V. A. 2003. Novel method to control pathogenic bacteria on human mucous membranes. Ann. N.Y. Acad. Sci. 987:207-214; Fischetti, V. A. 2001. Phage antibacterials make a comeback. Nature Biotechnol. 19:734-735). Although the range of bacteria targeted by lysins is less restrictive than the corresponding bacteriophage, lysins still maintain a degree of specificity, having minimal effects on other bacteria including commensal organisms. While bacteriophage host ranges are largely restrictive, recognizing only one specific antigen on its bacterial host, phage lysins are less restrictive, recognizing a specific carbohydrate molecule common to the particular species of host bacteria.

Bacterial resistance to phage lysins is believed to be less likely to arise as compared with bacteriophage adsorption for at least two reasons: first, bacterial lysis upon exposure to lysin is almost immediate, not giving bacteria much possibility for mutation and second, lysins bind to highly conserved molecules in the bacterial cell wall that are under selective pressure not to mutate. In contrast, bacterial resistance to many antibiotics is often easily identified. Furthermore, the problem with lysogenic conversion is reduced or eliminated with phage lysins, and animal testing and treatment can be performed effectively using lysins.

There is an ongoing need for therapies and agents effective in the diagnosis and control of bacterial contamination, colonization and infection. In addition, compounds with bacteriocidal effects may be useful in the decontamination of bacteria on inanimate surfaces and objects. The bactiophage lytic enzymes provided are useful in providing agents useful in the detection or killing of Group B streptococci (GBS) bacteria.

SUMMARY

The present invention relates to bacterial lysins comprising a PlyGBS peptide variant having bacterial killing activity. For example, the PlyGBS peptide variant may be a PlyGBS mutant lysine having a lytic killing activity against a Group B streptococci bacteria that is greater than the killing activity of the PlyGBS peptide against the same bacteria.

Lysins with improved lytic activity against GBS cells compared to the lytic activity of PlyGBS enzyme (SEQ ID NO:1) are disclosed. Hyperactive PlyGBS mutant lysins may provide greater killing activity against GBS cells compared with the PlyGBS protein alone, as evidenced by both in vitro and in vivo testing. The lysins may be mutant lytic enzymes derived from PlyGBS protein lytic mutant enzymes using DNA mutagenesis methods applied to the plyGBS gene. Polypeo-PlyGBS mutant enzymes that display increased lytic activity against GBS protein are also identified and characterized.

The killing activity of PlyGBS lysins, such as PlyGBS mutant lysins, can be quantified by performing an in vitro bacterial killing assay described in Example 3 below, or by performing an in vivo bacterial killing assay described in Example 4 below. A hyperactive PlyGBS mutant may provide at least 1.5-fold to about 40-fold greater lytic activity than PlyGBS (SEQ ID NO:1) against GBS cells., at least about 14-fold to about 40-fold greater lytic activity, or at least about 25-fold to about 40-fold greater lytic activity. Hyperactive PlyGBS mutant lysins include those selected from the group: PlyGBS 86-6 (SEQ ID NO:2), PlyGBS 80 (SEQ ID NO:3), PlyGBS 90-8 (SEQ ID NO:4), PlyGBS 90-1 (SEQ ID NO:5), PlyGBS 94 (SEQ ID NO:8) and PlyGBS 95 (SEQ ID NO:9). PlyGBS (SEQ ID NO:1) contains an N-terminal [amino acid (aa) 1-107] endopeptidase domain, a central (aa 150-394) muramidase domain and a C-terminal region (aa 395-443). Mutant PlyGBS86-6 (SEQ ID NO:2) (SEQ ID NO:2) has one amino acid change from aspartic acid to glutamic acid (D374E). Mutant PlyGBS80 (SEQ ID NO:3) (aa 1-164) (SEQ ID NO:3) and PlyGBS90-8 (SEQ ID NO:4) (aa 1-138) (SEQ ID NO:4) are truncated mutants due to stop codons brought by nonsense mutations. PlyGBS90-1 (SEQ ID NO:5) (SEQ ID NO:5) was derived from an out-of-frame deletion which deleted bp 424-1255 in plyGBS gene and as a result, it encodes first 141 amino acids of PlyGBS plus extra 13 amino acids (DGHALTIQSRRNG) due to the frame shift of the C-terminal region (bp 1256-1332) of plyGBS gene. Hyperactive PlyGBS mutant PlyGBS94 (SEQ ID NO:8) (SEQ ID NO:8) contains the N-terminal endopeptidase domain (first 146 amino acids) and is similar to mutant PlyGBS90-8 (SEQ ID NO:4) (first 138 amino acids) (SEQ ID NO:4). A similar level of lytic activity was observed in these two mutants. PlyGBS95 (SEQ ID NO:9) (SEQ ID NO:9) has an in-frame deletion of central muramidase domain (deletion between aa 147-348).

The structures of certain PlyGBS mutant lysins are also disclosed. Several hyperactive PlyGBS mutants include truncation mutants that contain only the endopeptidase domain from the N-terminal region of PlyGBS and represent about one-third of the wild type PlyGBS (SEQ ID NO:1) in length. These mutants may have 25-40 fold increase in specific activities compared to PlyGBS, and also may have a similar activity spectrum against several streptococcal species. PlyGBS has two putative catalytic domains and a C-terminal undesignated domain. Comparison of the PlyGBS mutants PlyGBS95 (SEQ ID NO:9) (SEQ ID NO:9) and PlyGBS94 (SEQ ID NO:8) (SEQ ID NO:8) indicates that the deletion of the C-terminus has no significant effect on its specificity or on lytic activity. The hyperactive PlyGBS mutants PlyGBS94 (SEQ ID NO:8) (SEQ ID NO:8), PlyGBS90-1 (SEQ ID NO:5) (SEQ ID NO:5) and PlyGBS90-8 (SEQ ID NO:4) (SEQ ID NO:4) may have truncations in the central and C-terminal regions, and appear to be similar to lysozyme in that they only have a catalytic domain without a cell-wall binding domain. The endopeptidase domain present in these mutants is nearly identical to the CHAP domain recently identified in another lytic enzyme from GBS bacteriophage B30, PlyGBS (SEQ ID NO:1) (Pritchard, D. G., S. Dong, J. R. Baker, and J. A. Engler, "The bifunctional peptidoglycan lysin of *Streptococcus agalactiae* bacteriophage B30," Microbiology 150: 2079-2087 (2004)). However, the CHAP domain by itself in these truncated mutants is not only active against GBS, but is significantly increased in activity (from 25 to 40 fold) over the wild type PlyGBS (SEQ ID NO:1). Although CHAP domains are widely present in many phage lysins, none of these CHAP domains has been reported to have lytic activity without the association of a cell-wall binding domain.

Biochemical characteristics of the hyperactive PlyGBS mutants, such as storage stability and optimum pH, have been compared with PlyGBS (SEQ ID NO:1). The mutant PlyGBS90-1 (SEQ ID NO:5) (SEQ ID NO:5) has its optimum activity when salt concentration is 50-100 mM, while the optimum NaCl concentration for wild-type PlyGBS (SEQ ID NO:1) is around 200 mM. Notably, the mutant PlyGBS90-1 (SEQ ID NO:5) (SEQ ID NO:5) maintains lytic activity against all the *streptococcus* species that are sensitive to PlyGBS (SEQ ID NO:1), even though the PlyGBS90-1 (SEQ ID NO:5) (SEQ ID NO:5) mutant contains only one-third of the wild-type PlyGBS (SEQ ID NO:1).

The hyperactive PlyGBS mutants are more lytically active than PlyGBS and can kill GBS at a faster rate than wild-type PlyGBS, providing an advantage for future intrapartum therapy that would require time-effectiveness. Hyperactive PlyGBS mutants may be administered in vivo, resulting in reduction of GBS colonization. For example, the hyperactive PlyGBS mutant PlyGBS90-1 (SEQ ID NO:5) (SEQ ID NO:5) was used in mouse vaginal model to test the efficacy of reducing GBS colonization in vivo. A single dose of PlyGBS90-1 (SEQ ID NO:5) (SEQ ID NO:5) reduced the GBS colonization from 5.54 logs (about $3.5 \times 10^5$ cfu per mouse on average) before treatment to 1.68 logs (less than 50 cfu per mouse) 4 hrs post-treatment. Administration of hyperactive PlyGBS mutants in vivo may be used, for instance, to reduce the neonatal GBS infection during delivery, providing an alternative approach to replace intrapartum antibiotic prophylaxis.

Other systems, methods, features and advantages of the invention will be, or will become, apparent to one with skill in the art upon examination of the following figures and detailed description. It is intended that all such additional systems, methods, features and advantages be included within this description.

BRIEF DESCRIPTION OF THE DRAWINGS

The invention can be better understood with reference to the following drawings and description. The components in the figures are not necessarily to scale, and provide an illustration of certain aspects of the invention.

FIG. 1 is a table listing the PlyGBS sequence (SEQ ID NO:1) and sequences for various PlyGBS mutants described (SEQ ID NOS: 2-9).

FIG. 4 is a schematic diagram of PlyGBS and several truncated mutants.

FIG. 5A is a graph showing the relative activity of PlyGBS, PlyGBS90-1 (SEQ ID NO:5) and PlyGBS90-8 (SEQ ID NO:4) at 4° C.; FIG. 5B is a graph showing the stability of PlyGBS, PlyGBS90-1 (SEQ ID NO:5) and PlyGBS90-8 (SEQ ID NO:4) at 4° C. Store in 25% glycerol at −80° C.

FIG. 6A is a graph comparing the killing effect for PlyGBS and PlyGBS90-1 (SEQ ID NO:5) at different amounts (2, 10, 50, and 100 µg) of PlyGBS and PlyGBS90-1 (SEQ ID NO:5); FIG. 6B is a graph comparing the killing effect for PlyGBS and PlyGBS90-1 (SEQ ID NO:5) using the same amount of PlyGBS and PlyGBS90-1 (SEQ ID NO:5) (about 3,000 µg) in the in vitro viability.

DETAILED DESCRIPTION

Figure 2:
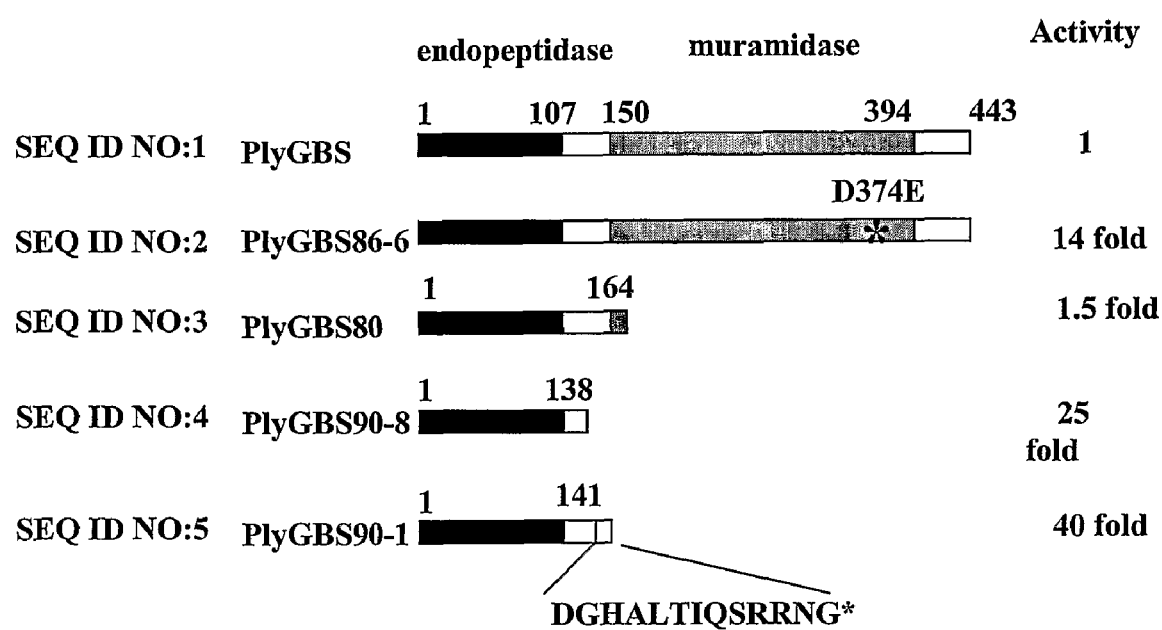
FIG. 2 is a schematic diagram of PlyGBS (SEQ ID NO:1) and several PlyGBS mutants having increased lytic activity against GBS cells.

Definitions of certain terms used and their applicability to the disclosure are provided below.

The term "hyperactive PlyGBS mutants" refers to PlyGBS mutant lysins with enhanced activity against GBS compared to PlyGBS enzyme under substantially identical testing conditions.

The term "isolated" means at least partially purified from a starting material.

The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciated that the amount of purification necessary will depend upon the use of the material.

For example, compositions intended for administration to humans ordinarily must be highly purified in accordance with regulatory standards.

The term "lytic enzyme genetically coded for by a bacteriophage" refers to a polypeptide having at least some lytic activity against the host bacteria.

"Polypeptide" refers to a molecule comprised of amino acids which correspond to polypeptides encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994).

"A native sequence phage associated lytic enzyme" refers to a polypeptide having the same amino acid sequence as an enzyme derived from nature. Such native sequence enzyme can be isolated from nature or can be produced by recombinant or synthetic means. The term "native sequence enzyme" specifically encompasses naturally occurring forms (e.g., alternatively spliced or modified forms) and naturally-occurring variants of the enzyme. In one example, the native sequence enzyme is a mature or full-length polypeptide that is genetically coded for by a gene from a bacteriophage specific for Group B streptococci (GBS).

The term "about" used with reference to a quantity includes variations in the recited quantity that are equivalent to the quantity recited, for instance an amount that is insubstantially different from a recited quantity for an intended purpose or function.

The term "effective amount" refers to an amount of an active ingredient sufficient to achieve a desired effect without causing an undesirable side effect. In some cases, it may be necessary to achieve a balance between obtaining a desired effect and limiting the severity of an undesired effect. The amount of active ingredient used will vary depending upon the type of active ingredient and the intended use of the composition of the present invention.

A "variant polypeptide sequence phage associated lytic enzyme" means a functionally active lytic enzyme genetically coded for by a bacteriophage specific for Group B streptococci (GBS), or Streptococcus agalactiae, having at least 50%, 55%, 60%, 65%, 70%, 75%, 80%, 85%, 90%, 95%, 97%, 98%, 99%, or even at least 99.5% amino acid sequence identity with a sequence described.

"Percent (%) polypeptide sequence identity" with respect to the lytic enzyme polypeptide sequences identified here is defined as the percentage of amino acid residues in a candidate sequence that are identical with the amino acid residues in the specific lytic enzyme polypeptide sequence, after aligning the sequences and introducing gaps, if necessary, to achieve the maximum percent sequence identity, and not considering any conservative substitutions as part of the sequence identity. Methods for alignment for purposes of determining percent amino acid sequence identity are described below.

PlyGBS Lysins

Bacteriophage lysins with killing activity against Group B streptococci (GBS) bacteria are provided. Preferred bacteriophage lysins are hyperactive PlyGBS mutant enzymes of PlyGBS lysin with enhanced killing activity against GBS compared to PlyGBS activity and its variants. Several hyperactive PlyGBS mutant enzymes with killing activity against GBS are identified and characterized in the examples described below. Other examples provide lysins with specific activity against other gram positive bacteria, which include variants and fragments of the lysins described.

The phage muralytic enzyme, PlyGBS, may be used to lyse GBS cells in vitro and in vivo, for example as described in Cheng, Q. et al., "Removal of group B streptococci colonizing the vagina and oropharynx of mice with a bacteriophage lytic enzyme," Antimicrob. Agents Chemother. 49: 111-117 (2005). PlyGBS belongs to a group of bacteriophage lysins that can kill bacteria by digesting the bacteria cell wall, making cells susceptible to osmotic lysis. For example, in a mouse model, a single dose of PlyGBS can significantly reduce GBS colonization in both the vagina and oropharynx. Administration of a phage muralytic enzyme such as PlyGBS is a promising alternative to intrapartum antibiotic prophylaxis in order to reduce vaginal GBS colonization in pregnant women before delivery, or to decontaminate newborns at various body sites, thus reducing the incidence of GBS-associated neonatal infections.

Lysins generally occur in a modular structure. The N-terminal module consists of a catalytic domain believed to possess the ability to break down the bacterial cell wall of certain bacteria. Ezymatic activities often associated with the catalytic domain are amidases, endopeptidases, glucosamidases and muramidases. The C-terminal module consists of a binding domain that is believed to have an affinity for a carbohydrate epitope on the target bacteria cell wall. The binding domain is believed to determine the specificity of the lysin.

Bacteriophage lytic agents effective against GBS bacteria are provided, along with corresponding polypeptide and polynucleotide sequences relating to the same. Compositions comprising the lytic enzymes provided may be useful in the diagnosis, treatment, and decontamination applications relating to several types of gram positive bacteria, as described, including GBS bacteria. Methods of treatment and decontamination using compositions comprising the lytic enzymes, polypeptides or polynucleotide sequences also are disclosed.

Hyperactive PlyGBS mutant enzymes exhibiting a lytic effect on BGS bacterial strains, and particularly, the lysins have killing activity against one or more GBS bacterial species are described. The lysins include hyperactive PlyGBS mutant lysins comprise a polypeptide sequence having at least 70%, 75%, 80%, 85%, 90%, 95%, 96%, 97%, 98%, 99% or greater homology to SEQ ID NO:2, SEQ ID NO:3, SEQ ID NO:4, SEQ ID NO:5, SEQ ID NO:8, or SEQ ID NO:9.

The following references relating to the therapeutic application of lytic enzymes as an antibacterial agent are incorporated herein by reference in their entirety: Cheng, Q., D. Nelson, S. W. Zhu, and V. A. Fischetti, "Removal of group B streptococci colonizing the vagina and oropharynx of mice with a bacteriophage lytic enzyme," Antimicrob. Agents Chemother. 49: 111-117 (2005); Loeffler, J. M., D. Nelson, and V. A. Fischetti. 2001. Rapid killing of *Streptococcus pneumoniae* with a bacteriophage cell wall hydrolase. Science 294: 2170-2172; Nelson, D., L. Loomis, and V. A. Fischetti. 2001. Prevention and elimination of upper respiratory colonization of mice by group A streptococci by using a bacteriophage lytic enzyme. Proc. Natl. Acad. Sci. USA 98: 4107-4112; and Schuch, R., D. Nelson, and V. A. Fischetti. 2002. A bacteriolytic agent that detects and kills *Bacillus anthracis*. Nature 418: 884-889.

The killing activity of PlyGBS lysins, such as PlyGBS mutant lysins, can be quantified by performing an in vitro bacterial killing assay described in Example 3 below, or by performing an in vivo bacterial killing assay described in Example 4 below.

Mutagenic PlyGBS Mutants

Referring to the table in FIG. 1, hyperactive PlyGBS mutant lysins include lysins selected from the group consisting of PlyGBS 86-6 (SEQ ID NO:2), PlyGBS 80 (SEQ ID NO:3), PlyGBS 90-8 (SEQ ID NO:4), PlyGBS 90-1 (SEQ ID NO:5), PlyGBS 94 (SEQ ID NO:8) and PlyGBS 95 (SEQ ID NO:9). FIG. 2 is a schematic diagram of PlyGBS and several mutants produced by random mutagenesis. PlyGBS (SEQ ID NO:1) contains an N-terminal [amino acid (aa) 1-107] endopeptidase domain, a central (aa 150-394) muramidase domain and a C-terminal region (aa 395-443). Mutant PlyGBS86-6 (SEQ ID NO:2) has one amino acid change from aspartic acid to glutamic acid (D374E). Mutant PlyGBS80 (SEQ ID NO:3) (aa 1-164) and PlyGBS90-8 (SEQ ID NO:4) (aa 1-138) are truncated mutants due to stop codons brought by nonsense mutations. PlyGBS90-1 (SEQ ID NO:5) came from an out-of-frame deletion which deleted bp 424-1255 in plyGBS gene and as a result, it encodes first 141 amino acids of PlyGBS plus extra 13 amino acids (DGHALTIQSRRNG) due to the frame shift of the C-terminal region (bp 1256-1332) of plyGBS gene.

Two hyperactive PlyGBS mutant lysins were obtained from mutator strain *E. coli* XL-1 Red. The first, PlyGBS86-6 (SEQ ID NO:2), has a single point mutation resulting in the amino acid change from aspartic acid to glutamic acid (D374E). The PlyGBS86-6 (SEQ ID NO:2) mutant has a specific activity 14 fold higher than wild type PlyGBS (SEQ ID NO:1). The second mutant, PlyGBS80 (SEQ ID NO:3), has a stop codon in the center of plyGBS gene (Q16Stop) resulting in a truncated molecule. The PlyGBS80 (SEQ ID NO:3) mutant contains only the first 163 amino acids of wild type PlyGBS (SEQ ID NO:1), but has a specific activity 1.5-fold higher than PlyGBS (SEQ ID NO:1).

Two hyperactive mutants were identified from PCR random mutagenesis. The mutant PlyGBS90-8 (SEQ ID NO:4) is similar to PlyGBS80 (SEQ ID NO:3) in that both are truncated mutants as a result of the incorporation of a stop codon. The PlyGBS90-8 (SEQ ID NO:4) mutant has the first 138 amino acids of PlyGBS (SEQ ID NO:1). Significantly, the PlyGBS90-8 (SEQ ID NO:4) mutant has a specific activity that is about 25-fold higher than the wild-type PlyGBS. Another mutant, PlyGBS90-1 (SEQ ID NO:5), does not include the region bp 424-1255 in the plyGBS gene. As a result, it encodes only the first 141 amino acids of PlyGBS (SEQ ID NO:1) plus an extra 13 amino acids due to the frame shift of the C-terminal region (bp 1256-1332) of plyGBS gene. This mutant has a specific activity that is about 40-fold higher than wild type.

Figure 3:
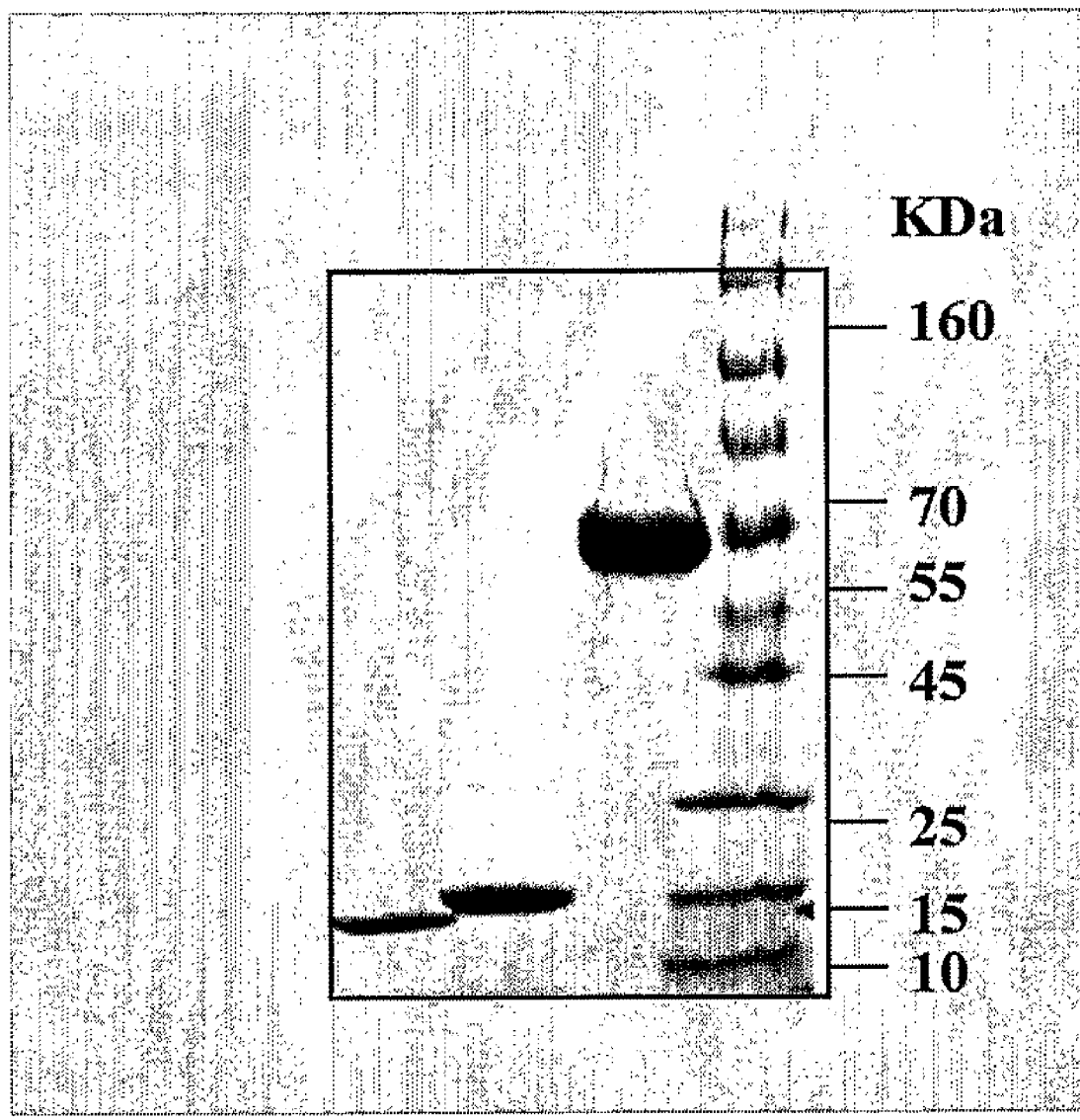
FIG. 3 is a commassie blue-stained SDS-PAGE gel (4-20% gradient) for purified PlyGBS90-8 (SEQ ID NO:4) (lane 1), PlyGBS90-1 (SEQ ID NO:5) (lane 2), and wild type PlyGBS (lane 3), with the molecular mass of the protein ladder is presented in kilodaltons (KDa).

The two hyperactive mutants, PlyGBS90-1 (SEQ ID NO:5) and PlyGBS90-8 (SEQ ID NO:4), were purified using Q-Sepharose anion exchange chromatography and the active fractions were pooled and analyzed on a gradient SDS-PAGE gel. As shown in FIG. 3, the PlyGBS90-1 (SEQ ID NO:5) and PlyGBS90-8 (SEQ ID NO:4) mutants migrated close to regions for calculated molecular weight (17.0, 15.3 KDa) listed in Table 1. FIG. 3 shows a commassie blue-stained SDS-PAGE gel (4-20% gradient) for purified PlyGBS90-8 (SEQ ID NO:4) (lane 1), PlyGBS90-1 (SEQ ID NO:5) (lane 2), and wild type PlyGBS (lane 3), with the molecular mass of the protein ladder presented in kilodaltons (KDa).

TABLE 1

Characteristics of wt PlyGBS and two hyperactive PlyGBS mutant lysins

| Protein | Total Amino acids | Calculated Molecular Weight (KDa) | Isoelectric Point (pI) |
|---|---|---|---|
| PLYGBS (SEQ ID NO: 1) | 443 | 49.6 | 4.88 |
| PLYGBS90-1 (SEQ ID NO: 5) | 154 | 17.0 | 4.99 |
| PLYGBS90-8 (SEQ ID NO: 4) | 138 | 15.3 | 4.50 |

PlyGBS Deletion Mutants

PlyGBS (SEQ ID NO:1) has two catalytic domains, an endopeptidase and a muramidase, and a C-terminal undesignated domain. (Cheng, Q., D. Nelson, S. W. Zhu, and V. A. Fischetti, "Removal of group B streptococci colonizing the vagina and oropharynx of mice with a bacteriophage lytic enzyme," Antimicrob. Agents Chemother. 49: 111-117 (2005)). Several of the PlyGBS mutants identified as hyperactive PlyGBS mutants are truncated mutants containing only one catalytic domain but still having higher activity than wild-type PlyGBS. Deletion mutants were designed based on the domain organization of PlyGBS. The deletion of C-terminus provides PlyGBS mutants that retain the specificity and lytic activity of the PlyGBS (SEQ ID NO:1) lytic enzyme. The deletion of C-terminus had no subtantial effect on its specificity or on lytic activity as illustrated by comparing the hyperactive deletion mutants PlyGBS95 (SEQ ID NO:9) and PlyGBS94 (SEQ ID NO:8). The hyperactive mutants (PlyGBS94 (SEQ ID NO:8), PlyGBS90-1 (SEQ ID NO:5), and PlyGBS90-8 (SEQ ID NO:4)) have truncations in the central and C-terminal regions, and appear to be similar to lysozyme in that they only have a catalytic domain without a cell-wall binding domain. However, no significant lytic activity was observed for egg white lysozyme (Sigma, St. Louis, Mo.) against GBS as well as many other bacterial species targeted by these truncated PlyGBS mutants. The endopeptidase domain present in these mutants is similar to the CHAP domain recently identified in the PlyGBS lytic enzyme (SEQ ID NO:1) from GBS bacteriophage B30. Pritchard et al., "The bifunctional peptidoglycan lysin of Streptococcus agalactiae bacteriophage B30," Microbiology. 150: 2079-2087 (2004). However, the CHAP domain by itself in the hyperactive PlyGBS truncated mutants is not only active against GBS, but is significantly increased in activity (from about 1.5 to about 40 fold) over the wild type PlyGBS (SEQ ID NO:1). Although CHAP domains are widely present in many phage lysins, CHAP domains do not typically have lytic activity without the association of a cell-wall binding domain.

FIG. 4 is a schematic diagram of PlyGBS and several truncated mutants. Mutant PlyGBS92 (SEQ ID NO:6) only contains central muramidase domain (aa 150-394), while PlyGBS93 (SEQ ID NO:7) has muramidase plus C-terminal domains (aa 150-443). Mutant PlyGBS94 (SEQ ID NO:8) contains the N-terminal endopeptidase domain (aa 1-146). For comparison, PlyGBS95 (SEQ ID NO:9) was constructed which has an in-frame deletion of central muramidase domain (deletion between aa 147-348). As shown in FIG. 4, hyperactive PlyGBS mutant PlyGBS94 (SEQ ID NO:8) contains the N-terminal endopeptidase domain (first 146 amino acids) and is similar to mutant PlyGBS90-8 (SEQ ID NO:4) (first 138 amino acids) obtained above. A similar level of lytic activity was observed in these two mutants. Mutant PlyGBS92 (SEQ ID NO:6) contains the putative muramidase domain located in the center of PlyGBS, while the PlyGBS93 (SEQ ID NO:7) mutant contains the muramidase domain plus the C-terminal region. Compared with the active endopeptidase domain present in mutant PlyGBS94 (SEQ ID NO:8), neither of these deletion mutants had any lytic activity against GBS. The lytic activity of a mutant (PlyGBS95 (SEQ ID NO:9)) containing an in-frame deletion of the central muramidase domain (FIG. 4) also was analyzed. The mutant has a lytic activity similar to mutant PlyGBS94 (SEQ ID NO:8).

Protein Stability of PlyGBS Hyperactive Mutants

FIG. 5A is a graph showing the relative activity of PlyGBS, PlyGBS90-1 (SEQ ID NO:5) and PlyGBS90-8 (SEQ ID NO:4) at 4° C. FIG. 5B is a graph showing the stability of PlyGBS (SEQ ID NO:1), PlyGBS90-1 (SEQ ID NO:5) and PlyGBS90-8 (SEQ ID NO:4) in 25% glycerol at 80° C. To obtain the data for the graphs in FIG. 5A and FIG. 5B, PlyGBS (SEQ ID NO:1) and hyperactive mutants PlyGBS90-1 (SEQ ID NO:5) and PlyGBS90-8 (SEQ ID NO:4) were stored in aliquots at 4° C. (FIG. 5A) in buffer and −80° C. (FIG. 5B) in 25% glycerol. At different time points, the lytic activity of these samples was measured by in vitro lytic activity against GBS and the Vmax values were determined to calculate relative activity. As shown in FIG. 5A, at 4° C., wild type PlyGBS is stable for more than 40 days, while only 25% and 31.2% activity was retained for the same period for mutant PlyGBS90-1 (SEQ ID NO:5) and PlyGBS90-8 (SEQ ID NO:4), respectively, and nearly lost at 60 days. However, when we stored these proteins in 25% glycerol at −80° C. (FIG. 5B), all 3 proteins had a better stability profile up to 40 days with less of a loss at 60 days.

Comparison of Lytic Activity of PlyGBS with Hyperactive PlyGBS Mutant Lysins

FIG. 6A and FIG. 6B are graphs showing a comparison of killing effect for PlyGBS and PlyGBS90-1 (SEQ ID NO:5) using different amounts of PlyGBS (SEQ ID NO:1) and mutant PlyGBS90-1 (SEQ ID NO:5) (2, 10, 50, and 100 μg) in an in vitro assay to measure the lytic activity by the determination of Vmax. To obtain the assay results illustrated in FIG. 6A, different amounts (2, 10, 50, and 100 μg) of PlyGBS (SEQ ID NO:1) and PlyGBS90-1 (SEQ ID NO:5) were used in the in vitro assay and the decrease of $OD_{600}$ was monitored by a spectrophotometer. The lytic activity was expressed as the initial velocity of the decrease in absorbance over time (−mOD600/min). As shown in FIG. 6A, the Vmax is only −22.8 $mOD_{600}$/min when 100 μg of wild type PlyGBS (SEQ ID NO:1) was used, while the Vmax values are −60.5 and −266.5 $mOD_{600}$/min for 10 μg and 100 μg of mutant PlyGBS90-1 (SEQ ID NO:5), respectively. Vmax measures the initial velocity of $OD_{600}$ drop, the rate of cell lysis, and is likely to be underestimated when 100 μg of hyperactive mutant PlyGBS90-1 (SEQ ID NO:5) is used because cell lysis occurred too rapidly to be measured accurately under this condition.

The efficacy of mutant PlyGBS90-1 (SEQ ID NO:5) in an in vitro cell viability assay was tested. To obtain the assay results illustrated in FIG. 6B, the same amount of PlyGBS (SEQ ID NO:1) and PlyGBS90-1 (SEQ ID NO:5) (about 3,000 μg) was used in the in vitro viability assay. As shown in FIG. 6B, cell viability decreased about 6 logs after 60 min incubation with mutant PlyGBS90-1 (SEQ ID NO:5), and only 2-logs for wild type PlyGBS over the same period. At 10 min incubation, the cell viability decreased 3 logs for the mutant and less than 1 log for the wild-type. These results indicate that the mutant enzyme has a significantly increased lytic activity against GBS.

Figure 7:
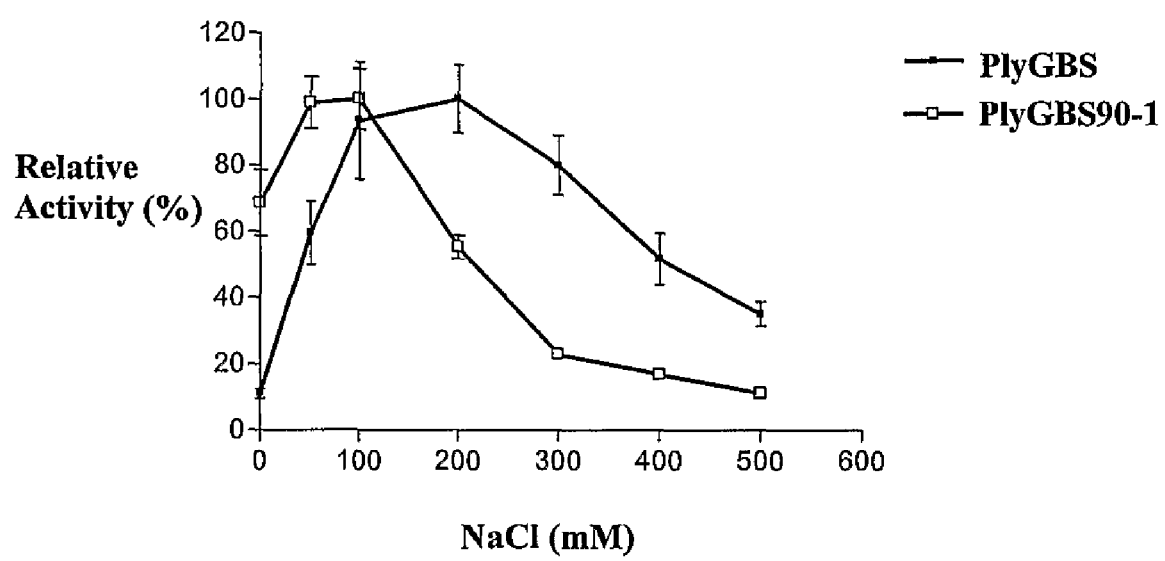
FIG. 7 is a graph showing the effect of salt concentration on enzymes' lytic activity.

Lysin activity of the PlyGBS lysins can be affected by the salt concentration. To obtain the results illustrated in the graph of FIG. 7, the lytic activity of PlyGBS (SEQ ID NO:1) and mutant PlyGBS90-1 (SEQ ID NO:5) were measured at various NaCl salt concentrations raging from 0 to 500 mM. FIG. 7 is a graph showing the effect of salt concentration on the lytic activity of PlyGBS (SEQ ID NO:1) and PlyGBS90-1 (SEQ ID NO:5) mutant. To obtain the data illustrated in FIG. 7, purified PlyGBS (SEQ ID NO:1) and PlyGBS90-1 (SEQ ID NO:5) were dialyzed against 2 mM Tris-HCl (pH7.4) overnight and various amounts of 5M NaCl were added to provide the desired salt concentration for the in vitro activity assay. The highest lytic activity under optimum salt concentration for PlyGBS (SEQ ID NO:1) or PlyGBS90-1 (SEQ ID NO:5) is considered as 100% for the standard to calculate relative activity. As shown in FIG. 7, the optimum NaCl concentration for wild type PlyGBS (SEQ ID NO:1) is about 200 mM, while the optimum for mutant PlyGBS90-1 (SEQ ID NO:5) shifted to about 50-100 mM. The results illustrated in FIG. 7 suggest that although the wild-type PlyGBS (SEQ ID NO:1) enzyme retained activity over a wider range of salt than the PlyGBS90-1 (SEQ ID NO:5) mutant, the mutant was more sensitive to these changes. When the pH activity profile of mutant PlyGBS90-1 (SEQ ID NO:5) was compared with wild-type PlyGBS (SEQ ID NO:1), both had a peak at pH 5.0.

Figure 8:
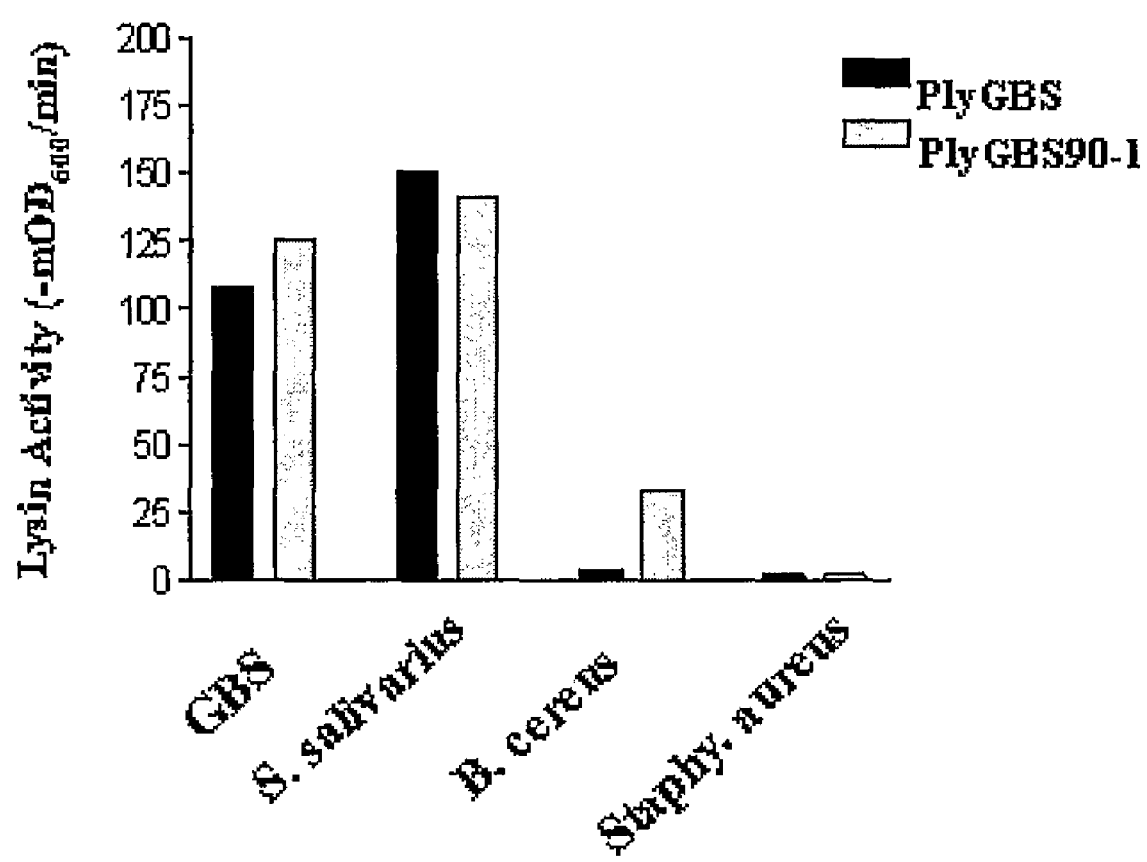
FIG. 8 is a graph showing lysin specificity of PlyGBS (SEQ ID NO:1) and PlyGBS90-1 (SEQ ID NO:5) in an in vitro assay.

The activity spectrum of mutant PlyGBS90-1 (SEQ ID NO:5) lysine was compared with wild-type PlyGBS (SEQ ID NO:1) lysine using the same amount of lysin. PlyGBS (SEQ ID NO:1) has a relatively broad spectrum against a number of streptococcal groups and species, such as *S. pyogenes* (GAS), *S. equi* (GCS) and *S. salivarius* (Cheng, Q., D. Nelson, S. W. Zhu, and V. A. Fischetti, "Removal of group B streptococci colonizing the vagina and oropharynx of mice with a bacteriophage lytic enzyme," Antimicrob. Agents Chemother. 49: 111-117 (2005), incorporated by reference herein in its entirety). FIG. 8 is a graph comparing the lysin specificity of PlyGBS (SEQ ID NO:1) and PlyGBS90-1 (SEQ ID NO:5). To obtain the data illustrated in FIG. 8, the same dose of PlyGBS or PlyGBS90-1 (SEQ ID NO:5) (40 U) was used in the in vitro assay and lytic activity was expressed as −mOD600/min. Surprisingly, both enzymes had a similar level of lytic activity (Vmax) against GBS and *S. salivarius* (FIG. 8) as well as some other streptococcal species. Other bacterial species were tested in which the wild type PlyGBS (SEQ ID NO:1) enzyme had little to no activity (i.e., *Staphylococcus aureus*, and *Bacillus cereus*), and the PlyGBS90-8 (SEQ ID NO:4) mutant enzyme demonstrated a similar pattern of specificity, except a small activity was found with *B. cereus* (FIG. 8). A similar result was observed with some of our other truncated mutants, such as PlyGBS80 (SEQ ID NO:3) and PlyGBS90-8 (SEQ ID NO:4), which show some killing effect against *B. cereus*.

Figure 9:
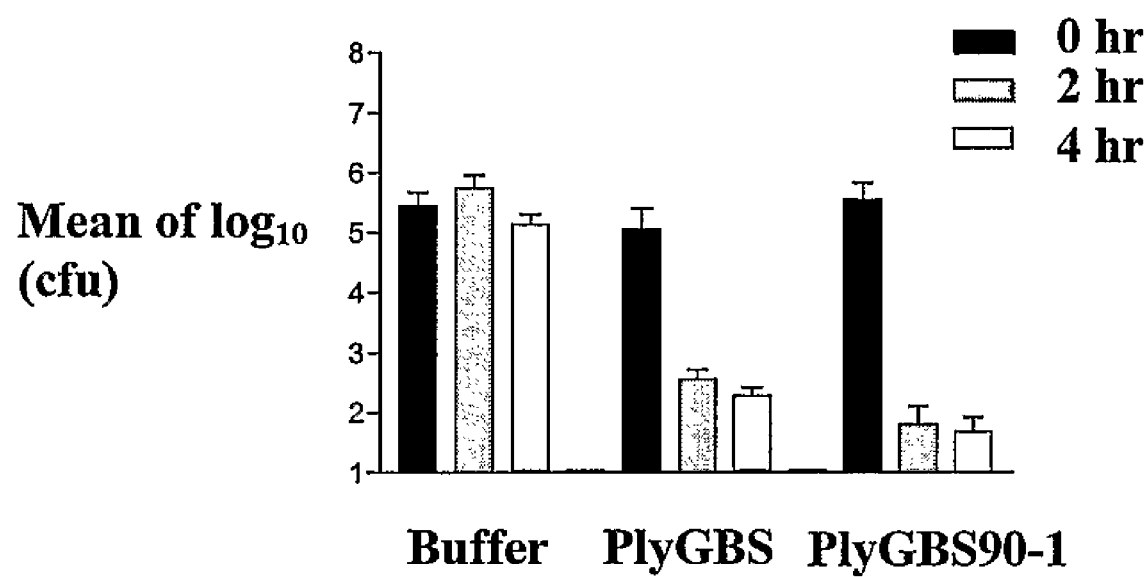
FIG. 9 is a graph showing the control of GBS colonization in mice vagina with PlyGBS (SEQ ID NO:1) or PlyGBS90-1 (SEQ ID NO:5).

The purified mutant PlyGBS90-1 (SEQ ID NO:5) preparation was tested for its lytic activity against GBS in a mouse vaginal model as described in the Examples below, and in Cheng, Q., D. Nelson, S. W. Zhu, and V. A. Fischetti, "Removal of group B streptococci colonizing the vagina and oropharynx of mice with a bacteriophage lytic enzyme," Antimicrob. Agents Chemother. 49: 111-117 (2005). FIG. 9 illustrates in vivo test results demonstrating the control of GBS colonization in mice vagina with PlyGBS (SEQ ID NO:1) or PlyGBS90-1 (SEQ ID NO:5). To obtain the data illustrated in FIG. 9, mice were colonized with GBS vaginally after synchronization with β-estradiol valerate. One day after GBS inoculation, three groups of mice were treated with either buffer (n=10), or 1,500 μg of PlyGBS (SEQ ID NO:1) (n=10), or 1,500 μg of PlyGBS90-1 (SEQ ID NO:5) (n=10). Each mouse was swabbed vaginally before treatment (0-hour samples) and after treatment at 2- to 4-hour intervals (2- and 4-hour samples). The colony counts of vaginal swabs were averaged for each time interval in the same group and plotted. Error bar represent the standard error of the mean. As shown in FIG. 9, mice treated with mutant PlyGBS90-1 (SEQ ID NO:5) showed a statistically significant drop (from 5.54 logs pre-treatment to an average of 1.68 logs after 4 hrs post-treatment) compared to buffer control (p<0.0001). Wild-type PlyGBS resulted in a drop of GBS from 5.38 logs to an average of 2.28 logs after 4 hrs post-treatment. Statistical analysis indicated that the mutant PlyGBS90-1 exhibited a more efficient decrease in GBS colonization that PlyGBS treatment 4 hours post-treatment (p=0.0037). Thus, the mutant PlyGBS90-1 (SEQ ID NO:5) exhibited a more efficient decrease in GBS colonization.

Variant Polypeptides

In addition to the lysins encoded by polypeptide sequences of SEQ ID NO: 1, the present disclosure also provides certain variant polypeptides, including fragments thereof and polypeptides with certain substitutions. The variant polypeptides may be hyperactive PlyGBS mutant lysins. For example, the variant polypeptide is a hyperactive PlyGBS mutant lysin selected from the group: PlyGBS 86-6 (SEQ ID NO:2), PlyGBS 80 (SEQ ID NO:3), PlyGBS 90-8 (SEQ ID NO:4), PlyGBS 90-1 (SEQ ID NO:5), PlyGBS 94 (SEQ ID NO:8) and PlyGBS 95 (SEQ ID NO:9). The modified or altered form of the protein or peptides and peptide fragments, as disclosed, include protein or peptides and peptide fragments that are chemically synthesized or prepared by recombinant DNA techniques, or both. These techniques include, for example, chimerization and shuffling. When the protein or peptide is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

A "variant polypeptide sequence phage associated lytic enzyme" may be an active lytic enzyme polypeptide having at least about 80% amino acid sequence identity with a full-length native sequence lytic enzyme polypeptide sequence as disclosed. Such lytic enzyme polypeptide variants include, for example, lytic enzyme polypeptides where one or more amino acid residues are added, or deleted, at the N- or C-terminus of the full-length native amino acid sequence. A lytic enzyme polypeptide variant will have at least about 80% amino acid sequence identity, and may have at least about 81%, 82%, 83%, 84%, 85%, 86%, 87%, 88%, 89%, 90%, 91%, 92%, 93%, 94%, 95%, 96%, 97%, 98%, 99%, or 99.5% amino acid sequence identity with a full-length native sequence lytic enzyme polypeptide sequence, a lytic enzyme polypeptide sequence lacking the signal peptide, an extracellular domain of a lytic enzyme polypeptide, with or without the signal peptide, or any other specifically defined fragment of a full-length lytic enzyme polypeptide sequence as disclosed. Lytic enzyme variant polypeptides may be at least about 10 amino acids in length, often at least about 20, 30, 40, 50, 60, 70, 80, 90, 100, 150, 200 or 300 amino acids in length, or more.

Such phage associated lytic enzyme variants include, for instance, lytic enzyme polypeptides where one or more amino acid residues are added, or deleted at the N or C terminus of the sequence of SEQ ID Nos. 1-9. In an example, one or more amino acids are substituted, deleted, and/or added to any position(s) in the sequence, or sequence portion.

"Percent amino acid sequence identity" with respect to the phage associated lytic enzyme sequences identified is defined as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available computer software such as blast software.

Polypeptide alignment for purposes of determining percent amino acid sequence identity can be achieved in various ways that are within the skill in the art, for example using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The percent amino acid sequence identity values also may be obtained as described below by using the WU-BLAST-2 computer program (Altschul et al., Methods in Enzymology 266:460-480 (1996)). Most of the WU-BLAST-2 search parameters are set to the default values. Those not set to default values are set with the following values: overlap span=1, overlap fraction=0.125, word threshold (T)=11, and scoring matrix=BLOSUM62. When WU-BLAST-2 is employed, a percent amino acid sequence identity value is determined by dividing (a) the number of matching identical amino acid residues between the amino acid sequence of the lytic enzyme polypeptide of interest having a sequence derived from the native lytic enzyme polypeptide and the comparison amino acid sequence of interest (i.e., the sequence against which the lytic enzyme polypeptide of interest is being compared which may be a lytic enzyme variant polypeptide) as determined by WU-BLAST-2 by (b) the total number of amino acid residues of the lytic enzyme polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the lytic enzyme polypeptide of interest.

Percent amino acid sequence identity may also be determined using the sequence comparison program NCBI-BLAST2 (Altschul et al., Nucleic Acids Res. 25:3389-3402 (1997)). The NCI-BLAST2 sequence comparison program may be downloaded from ncbi.nlm.nih.gov. NCBI-BLAST2 uses several search parameters, where all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and sorting matrix=BLOSUM62.

In situations where NCBI-BLAST2 is employed for amino acid sequence comparisons, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the percent amino acid sequence identity of A to B will not equal the percent amino acid sequence identity of B to A.

Lysin Fragments

In some examples, biologically active fragments of the lysins, including the polypeptide sequences such as SEQ ID NO: 1 or variants thereof described, are provided. The variant polypeptides include hyperactive PlyGBS mutant lysins. The variant polypeptide may a hyperactive PlyGBS mutant lysin selected from the group consisting of: PlyGBS 86-6 (SEQ ID NO:2), PlyGBS 80 (SEQ ID NO:3), PlyGBS 90-8 (SEQ ID NO:4), PlyGBS 90-1 (SEQ ID NO:5), PlyGBS 94 (SEQ ID NO:8) and PlyGBS 95 (SEQ ID NO:9). A "fragment" may include a variant polypeptide having an amino acid sequence that entirely is the same as part but not all of the amino acid sequence of the aforementioned polypeptides. A fragment may be "free-standing," or comprised within a larger polypeptide of which they form a part or region, most preferably as a single continuous region, a single larger polypeptide.

Biologically active portions of a protein or peptide fragment of the examples, as described, include polypeptides comprising amino acid sequences sufficiently identical to or derived from the amino acid sequence of the phage protein of the disclosure, which include fewer amino acids than the full length protein of the phage protein and exhibit at least one activity of the corresponding full length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide.

Fragments may include, for example, truncation polypeptides having a portion of an amino acid sequence corresponding to (e.g., 50% sequence identity, at least 60%, at least 70% sequence identity, at least 80% sequence identity, at least 95% sequence identity, at least 97% sequence identity or at least or even 98% sequence identity of at least 50 amino acid long region of the Natural Binding Region, or of variants, such as a continuous series of residues that includes the amino terminus, or a continuous series of residues that includes the carboxyl terminus. Degradation forms of the polypeptides in a host cell also are provided. Further provided are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also provided are fragments that have binding activities of at least $10^6$, $10^7$, $10^8$ or $10^9$ against GBS bacteria, including those with a similar activity or an improved activity, or with a decreased undesirable activity. Also advantageous are conjugates of binding site and a detectable tag or bacteriocidal tag that confers such desirable clinical function whereby the binding region specifically binds to a bacterial wall.

Variants that are fragments of the polypeptides of the disclosure may be employed for producing the corresponding full-length polypeptide by peptide synthesis; therefore, these variants may be employed as intermediates for producing the full-length polypeptides of examples of the disclosure.

Lytic enzyme peptide fragments may be prepared by any of a number of conventional techniques. Desired peptide fragments may be chemically synthesized An alternative approach involves generating lytic enzyme fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, lytic enzyme polypeptide fragments share at least one biological and/or immunological activity with the native lytic enzyme polypeptide disclosed.

For example, libraries of fragments of the coding sequence of a polypeptide of the disclosure can be used to generate a variegated population of polypeptides for screening and subsequent selection of variants. For example, a library of coding sequence fragments can be generated by treating a double stranded PCR fragment of the coding sequence of interest with a nuclease under conditions where nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high through put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811 7815; Delgrave et al. (1993) Protein Engineering 6(3):327 331).

Immunologically active portions of a protein or peptide fragment can include regions that bind to antibodies that recognize the phage enzyme. In this context, the smallest portion of a protein (or nucleic acid that encodes the protein) may be an epitope that is recognizable as specific for the phage that makes the lysin protein. Accordingly, the smallest polypeptide (and associated nucleic acid that encodes the polypeptide) that can be expected to bind antibody and is useful may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as epitopes, shorter sequences of 5, 6, or 7 amino acids long can exhibit epitopic structure in some conditions and have value. Thus, the smallest portion of the protein described by SEQ ID No. 1 may include polypeptides as small as 5, 6, 7, 8, 9, or 10 amino acids long.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules, that may be homologous specifically are intended as examples, and are not limiting. The homology of such valuable regions may be at least 50%, 65%, 75%, 85%, at least 90%, 95%, 97%, 98%, or at least 99% compared to SEQ ID No. 1. These percent homology values do not include alterations due to conservative amino acid substitutions.

An epitope as described may be used to generate an antibody and also can be used to detect binding to molecules that recognize the lysin protein. Another example is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). The specific binding may be at least $10^2$, $10^3$, $10^4$, $10^5$, $10^6$, $10^7$, $10^8$, or even higher than that for serum albumin under the same conditions.

In one example, the antibody or antibody fragment is in a form useful for detecting the presence of the lysin protein. A variety of forms and methods for their synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example. The antibody or antibody fragment may be synthesized via cell culture after genetic recombination. The antibody or antibody fragment may be prepared by a combination of cell synthesis and chemical modification.

Variant Polypeptides

Substitutional variants are those in which at least one residue in the amino acid sequence has been removed and a different residue inserted in its place. Such substitutions may be made in accordance with the following Table 2 when it is desired to finely modulate the characteristics of the protein. Table 2 shows amino acids which may be substituted for an original amino acid in a protein and which are regarded as conservative substitutions.

TABLE 2

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |

TABLE 2-continued

| Original Residue | Conservative Substitutions |
| --- | --- |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 2, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the lytic protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above.

Substantial modifications in function or immunological identity of the lytic enzyme polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions may entail exchanging a member of one of these classes for another class. Such substituted residues also may be introduced into the conservative substitution sites or, into the remaining (non-conserved) sites.

Polypeptide variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the lytic enzyme variant DNA.

Scanning amino acid analysis may also be employed to identify one or more amino acids along a contiguous sequence. For example, scanning amino acids may be relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science. 244: 1081-1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol. 150:1 (1976)]. If alanine substitution does not yield adequate amounts of variant, an isoteric amino acid can be used.

Chimeric Fusion Proteins

In some examples, a lysin also may be modified to form a chimeric molecule comprising a lytic enzyme fused to another, heterologous polypeptide or amino acid sequence. A "chimeric protein" or "fusion protein" comprises all or (for example, a biologically active) part of a polypeptide of the disclosure operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also are used to treat a bacterial infection by cleaving the cell wall in more than one location.

In one example, such a chimeric molecule comprises a fusion of the lytic enzyme with a tag polypeptide which provides an epitope to which an anti-tag antibody can selectively bind. The epitope tag is generally placed at the amino- or carboxyl-terminus of the lytic enzyme. The presence of such epitope-tagged forms of the lytic enzyme may be detected using an antibody against the tag polypeptide. Also, provision of the epitope tag enables the lytic enzyme to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)1; and the Herpes Simplex virus glycoprotein D (gD) tag and its antibody [Paborsky et al., Protein Engineering: (6):547-553 (1990)]. Other tag polypeptides include the Flag-peptide [Hopp et al., BioTechnology, 6:1204-1210 (1988)]; the KT3 epitope peptide [Martin et al., Science 255: 192-194 (1992)]; an α-tubulin epitope peptide (Skinner et al., J. Biol. Chem., 266:15163-15166 (1991)1; and the T7 gene 10 protein peptide tag (Lutz-Freyermuth et al., Proc. Natl. Acad. Sci. USA, 87:6393-6397 (1990)].

In an alternative example, the chimeric molecule may comprise a fusion of the lytic enzyme with an immunoglobulin or a particular region of an immunoglobulin. For a bivalent form of the chimeric molecule (also referred to as an "immunoadhesin"), such a fusion could be to the Fc region of an IgG molecule. The Ig fusions may include the substitution of a soluble (transmembrane domain deleted or inactivated) form of a lytic enzyme polypeptide in place of at least one variable region within an Ig molecule. The immunoglobulin fusion may include the hinge, C2 and CH3, or the hinge, CH1, CH2 and CH3 regions of an IgG1 molecule. For the production of immunoglobulin fusions see also U.S. Pat. No. 5,428,130 issued Jun. 27, 1995.

In another example, the chimeric protein or peptide contains a heterologous signal sequence at its N terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

Another example of a useful fusion protein is a GST fusion protein in which the polypeptide of the disclosure is fused to the C terminus of a GST sequence. Such a chimeric protein can facilitate the purification of a recombinant polypeptide of the disclosure.

Another example shows an immunoglobulin fusion protein in which all or part of a polypeptide of the disclosure is fused to sequences derived from a member of the immunoglobulin protein family. An immunoglobulin fusion protein can be incorporated into a pharmaceutical composition and administered to a subject to inhibit an interaction between a ligand (soluble or membrane bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial associated diseases and disorders for modulating (i.e., promoting or inhibiting) cell survival. Moreover, an immunoglobulin fusion protein of the disclosure can be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure can be produced by standard recombinant DNA techniques.

In another example, the fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the disclosure can be cloned into such an expression vector such that the fusion moiety is linked in frame to the polypeptide of the disclosure.

Combination with Signal Sequences

A signal sequence of a polypeptide of can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. The described polypeptides can further comprise a signal sequence, as well as to the signal sequence itself and to the polypeptide in the absence of the signal sequence (i.e., the cleavage products). In one example, a nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence, which facilitates purification, such as with a GST domain.

In another example, a signal sequence can be used to identify regulatory sequences, i.e., promoters, enhancers, repressors. Since signal sequences are the most amino terminal sequences of a peptide, it is expected that the nucleic acids which flank the signal sequence on its amino terminal side will be regulatory sequences that affect transcription. Thus, a nucleotide sequence which encodes all or a portion of a signal sequence can be used as a probe to identify and isolate the signal sequence and its flanking region, and this flanking region can be studied to identify regulatory elements therein. Variants of the polypeptides of the disclosure can have an altered amino acid sequence and can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one example, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

Shuffled Enzymes

Certain examples provide shuffled proteins or peptides comprising one or more lytic enzyme peptides or variants disclosed, gene products, or peptides for more than one related phage protein or protein peptide fragments that are randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970. (Method of shuffling polynucleotides); Kauffman, U.S. Pat. No. 5,976,862 (Evolution via Condon based Synthesis) and Huse, U.S. Pat. No. 5,808,022 (Direct Codon Synthesis). The contents of these patents are incorporated herein by reference. Shuffling is used to create a protein that is 10 to 100 fold more active than the template protein. The template protein is selected among different varieties of lysin or holin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA RNA hybrid, antisense RNA, Ribozymes, ESTs, SNIPs and other oligonucleotide based molecules that either alone or in combination with other molecules produce an oligonucleotide molecule capable or incapable of translation into a peptide. α

Covalent Modification of Polypeptides

Other examples provide for covalent modifications of a lytic enzyme, or fragment or variant thereof. One type of covalent modification includes reacting targeted amino acid residues of a lytic enzyme polypeptide with an organic derivatizing agent that is capable of reacting with selected side chains or the N- or C-terminal residues of the lytic enzyme-Derivatization with bifunctional agents is useful, for instance, for crosslinking lytic enzyme to a water-insoluble support matrix or surface for use in the method for purifying anti-lytic enzyme antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl-)dithiolpropioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp 79-86 (1983)], acetylation of the N-terminal amine, and amidation of any C-terminal carboxyl group.

Another type of covalent modification of the lytic enzyme polypeptide provided comprises altering the native glycosylation pattern of the polypeptide. Altering the native glycosylation pattern is intended for purposes herein to mean deleting one or more carbohydrate moieties found in native sequence lytic enzyme (either by removing the underlying glycosylation site or by deleting the glycosylation by chemical and/or enzymatic means), and/or adding one or more glycosylation sites that are not present in the native sequence lytic enzyme. In addition, the phrase includes qualitative changes in the glycosylation of the native proteins, involving a change in the nature and proportions of the various carbohydrate moieties present.

Addition of glycosylation sites to the lytic enzyme polypeptide may be accomplished by altering the amino acid sequence. The alteration may be made, for example, by the addition of, or substitution by, one or more serine or threonine residues to the native sequence lytic enzyme (for O-linked glycosylation sites). The lytic enzyme amino acid sequence may optionally be altered through changes at the DNA level, particularly by mutating the DNA encoding the lytic enzyme polypeptide at preselected bases such that codons are generated that will translate into the desired amino acids.

Another means of increasing the number of carbohydrate moieties on the lytic enzyme polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

Removal of carbohydrate moieties present on the lytic enzyme polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of lytic enzyme comprises linking the lytic enzyme polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

Holin Proteins

Bacterial lysins my optionally comprise or be administered in combination with holing proteins. Holin proteins may be administered, for example, in combination with one or more lytic enzyme peptides, or variants or fragments thereof. Holin proteins produce holes in the cell membrane, also may be used. Holin proteins, or "holins," can form lethal membrane lesions. Like the lytic proteins, holin proteins are coded for and carried by a phage. Most holin protein sequences are short, and overall, hydrophobic in nature, with a highly hydrophilic carboxy terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions.

Holins can be grouped into two general classes based on primary structure analysis. Class I holins are usually 95 residues or longer and may have three potential transmembrane domains. Class II holins are usually smaller, at approximately 65-95 residues, with the distribution of charged and hydrophobic residues indicating two TM domains (Young, et al. Trends in Microbiology v. 8, No. 4, March 2000). At least for the phages of gram positive hosts, however, the dual component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ 1, *LactoBacillus gasseri* bacteriophage Nadh, *Staphylococcus aureus* bacteriophage Twort, *Listeria monocytogenes* bacteriophages, *pneumococcal* phage Cp 1, *Bacillus subtillis* phage M29, *LactoBacillus delbrueckki* bacteriophage LL H lysin, and bacteriophage N11 of *Staphyloccous aureus*. (Loessner, et al., Journal of Bacteriology, August 1999, p. 4452 4460).

Polynucleotides

A lysin may be produced by any number of different methods. The lytic enzyme is produced by infecting said GBS bacteria with the genetic code delivered by a bacteriophage specific for said GBS bacteria. In another example, the lytic enzyme is produced by recombinant production from a nucleic acid that comprises a DNA having the sequence of bases of a polynucleotide sequence coding for one or more polypeptides of SEQ ID NO: 1 or a sequence that hybridizes with the complement of bases of a polynucleotide sequence coding for the polypeptide sequences of SEQ ID NO: 1 under suitable hybridization conditions. The lytic enzyme may be produced by removing a gene for the lytic enzyme from the phage genome, introducing said gene into a transfer vector, and cloning said transfer vector into an expression system, where the transfer vector is a plasmid. The expression system may be a bacteria, selected from any of the above listed groups, or, from *E. coli*. In another expression system production of the enzyme is by cell free expression system.

In addition to the full-length native polynucleotide sequences encoding lytic enzyme polypeptides described, it is contemplated that lytic enzyme variants can be prepared. The degeneracy of the genetic code further widens the scope of the examples as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Lytic enzyme variants can be prepared, for example, by introducing appropriate nucleotide changes into the lytic enzyme DNA, and/or by synthesis of the desired lytic enzyme polypeptide. Those skilled in the art will appreciate that amino acid changes may alter post-translational processes of the lytic enzyme, such as changing the number or position of glycosylation sites or altering the membrane anchoring characteristics.

One skilled in the art will recognize that the DNA mutagenesis techniques described here can produce a wide variety of DNA molecules that code for a bacteriophage lysin specific for GBS bacteria yet that maintain the essential characteristics of the lytic protein. Newly derived proteins also may be selected in order to obtain variations on the characteristic of the lytic protein, as will be more fully described below. Such derivatives include those with variations in amino acid sequence including minor deletions, additions and substitutions. While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known. Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct.

"Percent nucleic acid sequence identity" with respect to the phage associated lytic enzyme sequences means as the percentage of nucleotides in a candidate sequence that are identical with the nucleotides in the phage associated lytic enzyme sequence, after aligning the sequences and introducing gaps, if necessary, to achieve the maximum percent sequence identity. Alignment for purposes of determining percent nucleic acid sequence identity can be achieved in various ways that are within the scope of those skilled in the art, including but not limited to the use of publicly available computer software.

In addition to nucleotide sequences that code for lytic enzyme genetically coded for by a bacteriophage specific for GBS and fragments of those enzymes, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated by this disclosure are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

A large variety of isolated cDNA sequences that encode phage associated lysing enzymes and partial sequences that hybridize with such gene sequences are useful for recombinant production of the lysing enzyme. Representative nucleic acid sequences in this context are polynucleotide sequences coding for the polypeptides of SEQ ID NOS:1-9, sequence and sequences that hybridize, under stringent conditions, with complementary sequences of the DNA encoding the these polypeptide sequences. Still further variants of these sequences and sequences of nucleic acids that hybridize with those shown in the Figures also are contemplated for use in production of lysing enzymes according to the disclosure, including natural variants that may be obtained.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci.

USA 85:4397-4401) (incorporated herein by reference), and the ligase-mediated detection procedure (Landegren et al., 1988).

Many of the contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed and which differ from those disclosed by the deletion, addition or substitution of nucleotides while still encoding a protein which possesses the functional characteristic of the BSMR protein are contemplated by the disclosure. Also included are small DNA molecules which are derived from DNA molecules encoding all or part of the disclosed peptide sequences, or variants thereof. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage specific for GBS bacteria and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above also may be defined as DNA sequences which hybridize under stringent conditions to the DNA sequences disclosed, or fragments thereof.

Oligonucleotides specific to normal or mutant sequences are chemically synthesized using commercially available machines, labeled radioactively with isotopes (such as $^{32}$P) or non-radioactively (with tags such as biotin (Ward and Langer et al. Proc. Natl. Acad. Sci. USA 78:6633-6657 1981) (incorporated herein by reference), and hybridized to individual DNA samples immobilized on membranes or other solid supports by dot-blot or transfer from gels after electrophoresis. The presence or absence of these specific sequences are visualized by methods such as autoradiography or fluorometric or calorimetric reactions (Gebeyehu et al. Nucleic Acids Res. 15:4513-4534 1987) (incorporated herein by reference).

Sequence differences between normal and mutant forms of the gene also may be revealed by the direct DNA sequencing method of Church and Gilbert (1988) (incorporated herein by reference). Cloned DNA segments may be used as probes to detect specific DNA segments. The sensitivity of this method is greatly enhanced when combined with PCR (Stoflet et al. Science 239:491-494, 1988) (incorporated herein by reference). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags. Such sequences are useful for production of lytic enzymes according to examples described.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11, (herein incorporated by reference).

An example of such calculation is as follows: A hybridization experiment may be performed by hybridization of a DNA molecule (for example, a natural variation of the lytic enzyme genetically coded for by a bacteria specific for GBS bacteria) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic P (32) labeled-dCTP is carried out in a solution of high ionic strength such as 6 times SSC at a temperature that is 20-25 degrees Celsius below the melting temperature, Tm, (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to $10^9$ CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule.

The Tm of such a hybrid molecule may be estimated from the following equation: $T_m$=81.5 degrees C.-16.6 log 10 of sodium ion concentration)+0.41(% G+C)-0.63(% formamide)-(600/l) where l=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989), In Molecular Cloning: A Laboratory Manual, Cold Spring Harbor, N.Y. (incorporated herein by reference).

Thus, by way of example, of a 150 base pair DNA probe derived from the first 150 base pairs of the open reading frame of a cDNA having a % GC=45%, a calculation of hybridization conditions required to give particular stringencies may be made as follows:

Assuming that the filter will be washed in 0.3×SSC solution following hybridization, sodium ion=0.045M; % GC=45%; Formamide concentration=0 I=150 base pairs (see equation in Sambrook et al.) and so Tm=74.4 degrees C. The Tm of double-stranded DNA decreases by 1-1.5 degrees C. with every 1% decrease in homology (Bonner et al. (1973). J. Mol. Biol. 81:123). Therefore, for this given example, washing the filter in 0.3 times SSC at 59.4-64.4 degrees C. will produce a stringency of hybridization equivalent to 90%; DNA molecules with more than 10% sequence variation relative to the target BSMR cDNA will not hybridize. Alternatively, washing the hybridized filter in 0.3 times SSC at a temperature of 65.4-68.4 degrees C. will yield a hybridization stringency of 94%; DNA molecules with more than 6% sequence variation relative to the target BSMR cDNA molecule will not hybridize. The above example is given entirely by way of theoretical illustration. One skilled in the art will appreciate that other hybridization techniques may be utilized and that variations in experimental conditions will necessitate alternative calculations for stringency.

In some examples, stringent conditions may be defined as those under which DNA molecules with more than 25% sequence variation (also termed "mismatch") will not hybridize. In one example, stringent conditions are those under which DNA molecules with more than 15%, 10% or preferably 6% mismatch will not hybridize.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0-1% sodium pyrophosphate, 5×Denhardt's solution, sonicated salmon sperm DNA (50 □g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1.times.SSC at about 37-50° C. The skilled artisan will recognize how to adjust the temperature, ionic strength, etc. as necessary to accommodate factors such as probe length and the like.

Vectors/Host Cells Expressing Polynucleotides for Lysins

Vectors that comprise a polynucleotide or polynucleotides encoding one of the lysin polypeptide sequences described, or variants or fragments thereof, are also provided, including vectors formed from just the binding region, or as much as the entire lysin protein or ligation/conjugate of binding region with other protein. Other examples concern host cells that are genetically engineered with vectors of the disclosure and the production of polypeptides of the disclosure by recombinant techniques. Cell-free translation systems may also be employed to produce such proteins using RNAs derived from the DNA constructs of the disclosure.

For recombinant production, host cells can be genetically engineered to incorporate expression systems or portions thereof or polynucleotides of the disclosure. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *Streptococci, Staphylococci, Enterococci E. coli, Streptomyces* and *Bacillus subtilis* cells; fungal cells, such as yeast cells and *Aspergillus* cells; insect cells such as *Drosophila* S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the disclosure. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography is also employed for purification. Well known techniques for refolding protein may be employed to regenerate active conformation when the polypeptide is denatured during isolation and or purification.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Diagnostic Assays

Detection assays advantageously utilize a heterogeneous format where a binding reaction between a conjugated binding agent and an analyte occurs followed by a wash step to remove unbound conjugated binding agent. For example, gold sol particles may be prepared with protein that comprises the binding region with the binding protein immobilized on the particle surfaces. As binding occurs between the protein and bacteria, the particles merge and form a colored product. Analogously, the binding protein may be complexed, for example covalently with an enzyme such as beta galactosidase, peroxidase, or horseradish peroxidase. After wash, the remaining bound enzyme can be detected by adding a substrate such as a fluorogenic or chemilumigenic substrate. The binding protein may be complexed with any other reagent that can make a signal such as a rare earth fluor and detected by time resolved fluorescence, a radioactive material and detected by radioactivity measurement, or a regular fluorescent tag, and detected by fluorescence.

The conjugation of the binding region with a detectable tag may be carried out by synthetic chemistry or a biological process. For example, a DNA sequence coding for the binding region or of the entire lysine protein can be linked to genetic information that encodes a detectable marker such as green fluorescent protein (GFP) or an enzyme such as alkaline phosphatase. This could be accomplished by separating the DNA for the binding domain by removing the N-terminal catalytic domain and replacing it in frame with indicator molecules such as green flourescent protein (GFP) and purifying the expressed fusion molecule for the identification of GBS bacteria. Since the binding domain has a similar binding affinity of an immunoglobulin G molecule, the marked binding domain will effectively identify GBS bacteria with little false positive activity. One also could fuse the GFP molecule or an enzyme at the 5' end of the whole lysin enzyme if necessary, by doing so the enzymatic domain will be at least partly inactivated, still allowing the binding domain to function to bind to its substrate in the cell wall.

The isolated binding domain separated from the catalytic domain may be expressed, purified and labeled using a number of fluorescent molecules such as fluorescein isothiocyanate, rhodamine isothiocyanate and others known by skilled artisans. The binding domain may be modified with biotin to allow formation of a biotin-avidin complex after the binding region adheres to the GBS bacteria for identification.

Other catalytic domains may be added to the binding region. As exemplified by Diaz et al. Proc. Natl. Acad. Sci. U.S.A., 87:8125 (1990) for another system, the catalytic domain may be replaced with catalytic domains from other phage lytic enzymes to cleave other bonds in the peptidoglycan cell wall of GBS bacteria. For example, the portion of the 5' end of the gamma lysin gene that codes for the N-terminal catalytic domain (an amidase) may be removed and replaced with the catalytic domain from phage lytic enzymes of other GBS phage and even from phage of other gram-positive and gram-negative bacteria. These catalytic domains may be other amidases (which may have higher activity or special features), muramidases, glucaminidases, or endopeptidases, all of which, when genetically fused to the binding domain of the gamma lysin will cleave their respective bonds in the peptidoglycan of the GBS bacteria. In a related example two or three (or more) tandem catalytic domains of different specificities may be fused (i.e., muramidases-glucaminidases-amidase) to a single gamma lysin binding domain to cleave these bonds in the GBS bacteria cell wall peptidoglycan producing a highly active cleaving enzyme. Navarre (Identification of a D alanyl glycine endopeptidase activity. J Biol. Chem. 1999 May 28; 274:15847 56.) has shown that triple enzymatic domains may exist in bacteriophage lytic enzymes.

Various conventional linkers can be used, e.g., diisocyanates, diisothiocyanates, carbodiimides, bis-hydroxysuccinimide esters, maleimide-hydroxysuccinimide esters, glutaraldehyde and the like, such as a selective sequential linker such as the anhydride-isothiocyante linker disclosed in U.S. Pat. No. 4,680,338.

Therapeutic Compositions

Lytic enzymes may also be used to provide a prophylactic treatment for conditions associated with exposure to GBS bacteria, or as a therapeutic treatment for those who have already become ill from infection. The phage associated lytic enzymes described are specific for GBS bacteria and preferably effectively and efficiently break down the cell wall of the GBS bacteria.

The lytic enzyme polypeptides described also may be employed as a therapeutic agent. The lytic enzyme polypeptides of the present invention can be formulated according to known methods to prepare pharmaceutically useful compositions, whereby the lytic enzyme product hereof is combined in admixture with a pharmaceutically acceptable carrier vehicle. Compositions which may be used for the prophylactic and therapeutic treatment of a GBS bacteria infection also includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Prior to, or at the time the modified lytic enzyme is put in the carrier system or oral delivery mode, the enzyme may be in a stabilizing buffer environment for maintaining a suitable pH range, such as between about 5.0 and about 8.0, including a pH of about 5.0, 6.0, 7.0, 8.0 or any pH interval of 0.05 therebetween, or any interval that is a multiple of 0.05 therebetween, including pH values of 5.2, 6.5, 7.4, 7.5 and 8.5.

Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

Any of the carriers for the lytic enzyme may be manufactured by conventional means. However, if alcohol is used in the carrier, the enzyme should be in a micelle, liposome, or a "reverse" liposome, to prevent denaturing of the enzyme. Similarly, when the lytic enzyme is being placed in the carrier, and the carrier is, or has been heated, such placement should be made after the carrier has cooled somewhat, to avoid heat denaturation of the enzyme. The carrier preferably is sterile. One or more lytic enzymes may be added to these substances in a liquid form or in a lyophilized state, whereupon it will be solubilized when it meets a liquid body.

Stabilizing Buffers

A stabilizing buffer should allow for the optimum activity of the lysin enzyme. The buffer may contain a reducing reagent, such as dithiothreitol. The stabilizing buffer also may be or include a metal chelating reagent, such as ethylenediaminetetracetic acid disodium salt, or it also may contain a phosphate or citrate phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable. Any number of chimeric and shuffled lytic enzymes, alone or along with holin proteins, may be assembled to treat the exposure to GBS bacteria.

Mucoadhesives

In some examples, a therapeutic composition comprises a mucoadhesive and a lytic enzyme, or chimeric and/or shuffled lytic enzymes, or their peptide fragments when the composition is directed to the mucosal lining to kill colonizing disease bacteria. The mucosal lining, as disclosed and described, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

For these and other reasons it is advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention.

J. R. Robinson (U.S. Pat. No. 4,615,697, incorporated herein by reference) provides a review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multi lamellar micelles also may be used to control the release of enzyme.

Other approaches involving mucoadhesives which are the combination of hydrophilic and hydrophobic materials, are known. Orahesive® from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present disclosure produce an insoluble copolymer.

U.S. Pat. No. 4,948,580, also incorporated by reference, describes a bioadhesive oral drug delivery system. The composition includes a freeze dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste like preparations comprising (A) a paste like base comprising a polyorganosiloxane and a water soluble polymeric material which are may be present in a ratio by weight from 3:6 to 6:3, and (B) an active ingredient. U.S. Pat. No. 5,554,380 claims a solid or semisolid bioadherent orally ingestible drug delivery system containing a water in oil system having at least two phases. One phase comprises from about 25% to about 75% by volume of an internal hydrophilic phase and the other phase comprises from about 23% to about 75% by volume of an external hydrophobic phase, where the external hydrophobic phase is comprised of three components: (a) an emulsifier, (b) a glyceride ester, and (c) a wax material. U.S. Pat. No. 5,942,243 describes some representative release materials useful for administering antibacterial agents, which disclosure is incorporated by reference.

A therapeutic composition may contain polymeric mucoadhesives consisting essentially of a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and where at least 10% of said total hydrophilic monomer is acidic, said graft copolymer when fully hydrated having an equilibrium water content of at least 90%.

Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

Mucoadhesivity of the compositions of these examples are, to a large extent, produced by the hydrophilic acidic monomers of the chain in the polystyrene graft copolymer. The acidic monomers include, but are not limited to, acrylic and methacrylic acids, 2 acrylamido 2 methyl propane sulfonic acid, 2 sulfoethyl methacrylate, and vinyl phosphonic acid. Other copolymerizable monomers include, but are not limited to N,N dimethylacrylamide, glyceryl methacrylate, polyethylene glycol monomethacrylate, etc.

The compositions of the disclosure may optionally contain other polymeric materials, such as poly(acrylic acid), poly,(vinyl pyrrolidone), and sodium carboxymethyl cellulose plasticizers, and other pharmaceutically acceptable excipients in amounts that do not cause a deleterious effect upon mucoadhesivity of the composition. The dosage forms of the compositions of this disclosure can be prepared by conventional methods.

Pharmaceuticals

The present disclosure also provides compositions comprising one or more pharmaceutical agents and one or more lysins. Further provided are methods of treatment combining administration of one or more pharmaceutical agents and one or more lysins administered separately or in combination.

Pharmaceuticals that may be used include antimicrobial agents, anti-inflammatory agents, antiviral agents, local anesthetic agents, corticosteroids, destructive therapy agents, antifungals, and antiandrogens. Active pharmaceuticals that may be used in topical formulations include antimicrobial agents, especially those having anti-inflammatory properties such as dapsone, erythromycin, minocycline, tetracycline, clindamycin, and other antimicrobials. Weight percentages for the antimicrobials are from about 0.5% to about 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. An exemplary concentration for local anesthetics is about 0.025% to about 5% by weight of the total composition. Anesthetics such as benzocaine also may be used at a preferred concentration of about 2% to about 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. The concentrations for corticosteroids such as hydrocortisone or methylprednisolone acetate may be from about 0.2% to about 5.0% by weight.

Destructive therapy agents such as salicylic acid or lactic acid also may be used. A concentration of about 2% to about 40% by weight may be used. Cantharidin is may be utilized, for example, in a concentration of about 5% to about 30% by weight. Typical antifungals that may be used in topical compositions and examples of suitable weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). Other topical agents may be included to address a variety of topical co-infections that may occur as will be appreciated by skilled artisans.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

The composition may comprise dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL®" gelling polymer, methylparaben, propylparaben, titanium dioxide, BHA, and a caustic material to neutralize the "CARBOPOL®"

In order to accelerate treatment of the infection, the therapeutic agent may further include at least one complementary agent that may also potentiate the bactericidal activity of the lytic enzyme. The complementary agent can be erythromycin, clarithromycin, azithromycin, roxithromycin, other members of the macrolide family, penicillins, cephalosporins, and any combinations thereof in amounts that are effective to synergistically enhance the therapeutic effect of the lytic enzyme. Virtually any other antibiotic may be used with the modified lytic enzyme. Similarly, other lytic enzymes may be included in the carrier to treat other bacterial infections. Holin proteins may be included in the therapeutic treatment.

In some examples, a mild surfactant in an amount effective to potentiate the therapeutic effect of the modified lytic enzyme may be used in or in combination with a therapeutic composition. Suitable mild surfactants include, inter alia, esters of polyoxyethylene sorbitan and fatty acids (Tween series), octylphenoxy polyethoxy ethanol (Triton X series), n Octyl beta.D glucopyranoside, n Octyl betaD thioglucopyranoside, n Decal beta D glucopyranoside, n Dodecyl betaD glucopyranoside, and biologically occurring surfactants, e.g., fatty acids, glycerides, monoglycerides, deoxycholate and esters of deoxycholate.

Administration of Compositions Comprising Lysins

Therapeutic compositions comprising one or more lytic enzymes, such as PlyGBS, or variants or fragments thereof, can be administered to a subject by any suitable means. Means of application of the lytic enzyme(s) (modified or unmodified) include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or any combination of these and similar methods of application. The forms in which the lytic enzyme may be administered include but are not limited to lozenges, troches, candies, injectants, chewing gums, tablets, powders, sprays, liquids, ointments, and aerosols. It is most probable that exposure to the GBS bacteria will be through the nose. It is best to be treated for exposure to the bacteria as soon as possible.

When the lytic enzyme(s) is introduced directly by use of nasal sprays, nasal drops, nasal ointments, nasal washes, nasal injections, nasal packing, bronchial sprays, oral sprays, and inhalers, the enzyme may be in a liquid or gel environment, with the liquid acting as the carrier. A dry anhydrous version of the modified enzyme may be administered by the inhaler and bronchial spray, although a liquid form of delivery also may be used.

The lozenge, tablet, or gum into which the enzyme is added may contain sugar, corn syrup, a variety of dyes, non sugar sweeteners, flavorings, any binders, or combinations thereof. Similarly, any gum based products may contain acacia, carnauba wax, citric acid, corn starch, food colorings, flavorings, non sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another example of the disclosure, sugar substitutes are used in place of dextrose, sucrose, or other sugars.

As noted above, the enzyme also may be placed in a nasal spray, where the spray is the carrier. The nasal spray can be a long acting or timed release spray, and can be manufactured by means well known in the art. An inhalant also may be used, so that the enzyme may reach further down into the bronchial tract, including into the lungs.

Any of the carriers for the lytic enzyme may be manufactured by conventional means. However, it is preferred that any mouthwash or similar type products not contain alcohol to prevent denaturing of the enzyme, although enzymes in liposomes and in other protective modes and forms may be used in alcohol. Similarly, when the enzyme(s) is (are) being placed in a cough drop, gum, candy or lozenge during the manufacturing process, such placement should be made prior to the hardening of the lozenge or candy but after the cough drop or candy has cooled somewhat, to avoid heat denaturation of the enzyme. The enzyme may also be sprayed over the surface of the cough drop gum, candy, or lozenge, in high enough dosages to be effective.

The enzyme may be added to these substances in a liquid form or in a lyophilized state, whereupon it will be solubilized when it meets body fluids such as saliva. The enzyme also may be in a micelle or liposome.

Dosage of Lysins

The effective dosage rates or amounts of the enzyme(s) to treat the infection will depend in part on whether the enzyme(s) will be used therapeutically or prophylactically, the duration of exposure of the recipient to the infectious bacteria, the size and weight of the individual, etc. The duration for use of the composition containing the enzyme also depends on whether the use is for prophylactic purposes, where the use may be hourly, daily or weekly, for a short time period, or whether the use will be for therapeutic purposes where a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme that may provide for an effective amount or dosage of enzyme may be in the range of about 10 units/ml to about 500,000 units/ml of fluid in the wet or damp environment of the nasal and oral passages, and topically as well and possibly in the range of about 10, 20, 30, 40, 50, 60, 70, 80, 90, or 100 units/ml to about 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. Thus, the number of dosages will be dependent upon the circumstances and can range from 1-4 times per day or more, with durations from one day to multiple weeks. Infections can occur in the skin and thus such compositions may be formulated for topical application as well, using well known vehicles such as those described in U.S. Pat. Nos. 6,056,954 and 6,056,955.

Methods of Treatment

There are a number of advantages to using lytic enzymes to treat bacterial infections, particularly GBS bacteria. The modular design of lysins, with their distinct catalytic and binding domains, makes them ideal for domain swapping experiments in which bacterial specificities and catalytic activities can be improved or adapted for use against alternate pathogens. Since the catalytic and binding targets of lysins (peptidoglycan and associated carbohydrates, respectively) are largely essential for viability, lysin resistance will be rare.

"Treatment" refers to both therapeutic treatment and prophylactic or preventative measures, where the object is to prevent or slow down (lessen) the targeted pathologic condition or disorder. Those in need of treatment include those already with the disorder as well as those prone to have the disorder or those in whom the disorder is to be prevented.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems. When treating an bacterial exposure or infection, the lytic enzyme may be administered in any suitable fashion, including parenterally or through the oral or nasal cavity.

Dosages and desired drug concentrations of pharmaceutical compositions of the present invention may vary depending on the particular use envisioned. The determination of the appropriate dosage or route of administration is well within the skill of an ordinary physician. Animal-experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a lytic enzyme is employed, normal dosage amounts may vary from about 10 ng/kg to up to 100 mg/kg of mammal body weight or more per day, or about 1 µg/kg/day to 10 mg/kg/day, depending upon the route of administration. Guidance as to particular dosages and methods of delivery is also provided below, as well as in the literature. It is anticipated that different formulations will be effective for different treatment compounds and different disorders, that administration targeting one organ or tissue, for example, may necessitate delivery in a manner different from that to another organ or tissue.

Where sustained-release administration of a lytic enzyme is desired in a formulation with release characteristics suitable for the treatment of any disease or disorder requiring administration of the lytic enzyme, microencapsulation of the lytic enzyme is contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems." in Vaccine Design The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins can use poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/ glycolide polymer," in: M. Chasin and R. Langer (Eds.), Biodegradable Polymers as DruI: Delivery Systems (Marcel Dekker: New York, 1990), pp. 1-41.

Cutaneous Infection

Compositions for treating topical infections comprise an effective amount of at least one lysin produced according to this disclosure and a carrier for delivering at least one lytic enzyme to the infected skin. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, where the enzyme is in a lyophilized form on the bandage. This method of application is most effective for the treatment of infected skin.

The carriers of topical compositions may comprise semi-solid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations that can aid in the exposure of the skin to a medicament.

Polymer thickeners that may be used include those known to one skilled in the art, such as hydrophilic and hydroalcoholic gelling agents frequently used in the cosmetic and pharmaceutical industries. The hydrophilic or hydroalcoholic gelling agent can comprise, for example, "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). The gelling agent may comprise between about 0.2% to about 4% by weight of the composition. More particularly, examples of the compositional weight percent range for "CARBOPOL®" may be between about 0.5% to about 2%, while the weight percent range for "NATROSOL®" and "KLUCEL®" may be between about 0.5% to about 4%. A compositional weight percent range for both "HYPAN®" and "STABILEZE®" may be between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other gelling polymers include hydroxyethylcellulose, cellulose gum, MVE/MA decadiene crosspolymer, PVM/MA copolymer, or a combination thereof.

Preservatives also may be used in this invention and may comprise, for example, about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

In one example, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. One exemplayer ratio of micro particulate to dissolved dapsone is five or less.

In another example, the invention comprises about 1% carbomer, about 80-90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL® 980" and the caustic material may include sodium hydroxide solution.

In one example, if there is a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. The lytic enzyme may be a lytic enzyme, a chimeric lytic enzyme, and/or shuffled lytic enzyme which may be used in conjunction with a holin protein or a combination thereof. The lytic enzyme may be in an environment having a pH which allows for activity of the lytic enzyme. If an individual has been exposed to someone with the upper respiratory disorder, the lytic enzyme will reside in the mucosal lining and prevent any colonization of the infecting bacteria.

Parenteral Administration

In some examples, an infection may be treated parenterally. The enzymes which can be used are, as above, lytic enzymes, chimeric lytic, enzymes, shuffled lytic enzymes, and combinations thereof. The enzymes can be administered intramuscularly, intravenously, subcutaneously, subdermally, or combinations thereof. In one example, infections may be treated by injecting into the patient a therapeutic agent comprising the appropriate shuffled and/or chimeric lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non aqueous vehicles such as fixed oils, liposomes, and ethyl oleate are also useful herein. Other phage associated lytic enzymes, along with a holin protein, may be included in the composition.

In cases where intramuscular injection is the chosen mode of administration, an isotonic formulation may be used. Generally, additives for isotonicity can include sodium chloride, dextrose, mannitol, sorbitol and lactose. In some cases, isotonic solutions such as phosphate buffered saline are used. Stabilizers include gelatin and albumin. In some examples, a vasoconstriction agent is added to the formulation. The pharmaceutical preparations are provided sterile and pyrogen free. Generally, as noted above, intravenous injection may be most appropriate.

The carrier suitably contains minor amounts of additives such as substances that enhance isotonicity and chemical stability. Such materials are non toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter ions such as sodium; non ionic surfactants such as polysorbates, poloxamers, or polyethylene glycol (PEG); and/or neutral salts, e.g., NaCl, KCl, $MgCl_2$, $CaCl_2$, etc.

Glycerin or glycerol (1,2,3 propanetriol) is commercially available for pharmaceutical use. Glycerin or glycerol may be diluted in sterile water for injection, or sodium chloride injection, or other pharmaceutically acceptable aqueous injection fluid, and used in concentrations of 0.1 to 100% (v/v), 1.0 to 50% or about 20%.

DMSO, is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The vehicle also may include Ringer's solution, a buffered solution, and dextrose solution, particularly when an intravenous solution is prepared.

Prior to, or at the time the enzyme is put in the carrier system or oral delivery mode, it may be desirable for the enzymes be in a stabilizing buffer environment, maintaining a pH range between about 5.0 and about 7.5.

The stabilizing buffer should allow for the optimum activity of the enzyme. The buffer may be a reducing reagent, such as dithiothreitol. The stabilizing buffer also may be or include a metal chelating reagent, such as ethylenediaminetetracetic acid disodium salt, or it also may contain a phosphate or citrate phosphate buffer. The buffers found in the carrier can serve to stabilize the environment for the lytic enzymes.

The effective dosage rates or amounts of the enzyme to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 10, 20, 30, 40, 50, 60, 70, 80, 90, or 100 units/ml to about 10,000,000 units/ml of composition, in a range of about 1000 units/ml to about 10,000,000 units/ml, and from about 10,000 to 10,000,000 units/ml. The amount of active units per ml and the duration of time of exposure depend on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. The concentration of the enzyme for the treatment is dependent upon the bacterial count in the blood and the blood volume.

In order to accelerate treatment of the infection, the therapeutic agent may further include at least one complementary agent which may also potentiate the bactericidal activity of the lytic enzyme. The complementary agent can be any antibiotic effective against GBS bacteria. Similarly, other lytic enzymes may be included to treat other bacterial infections.

Additionally, a number of methods can be used to assist in transporting the enzyme across the cell membrane. The enzyme can be transported in a liposome, with the enzyme be "inserted" in the liposomes by known techniques. Similarly, the enzyme may be in a reverse micelle. The enzyme may also be pegylated, attaching the polyethylene glycol to the non-active part of the enzyme. Alternatively, hydrophobic molecules can be used to transport the enzyme across the cell membrane. Finally, the glycosylation of the enzyme can be used to target specific internalization receptors on the membrane of the cell.

EXAMPLES

Materials

Restriction endonucleases were obtained from New England Biolabs (Beverly, Mass.). All reagents used were purchased from Sigma (St. Louis, Mo.) unless otherwise indicated. Bacteria strains and plasmids used in this study are listed in Table 3 at the end of the Examples.

Example 1

Cloning and Sequence Alignment of PlyGBS

Clones of the GBS phage NCTC11261 genomic library were screened for a possible lysin gene on a GBS NCTC11237 bacterial overlay. The full sequence of the lysin gene (plyGBS) was obtained by sequencing of the phage NCTC11261 genomic DNA. Similarity searches indicated that at both the nucleotide and amino acid level this gene was over 90% identical to several lysins from various streptococcal species, including GBS phage B30 lysin (SEQ ID NO:1) (GenBank accession number AAN28166), *Streptococcus pyogenes* M1 phage-associated lysin (MK33905), and *Streptococcus equi* phage-associated protein (AF186180).

Alignment of the putative PlyGBS protein sequence with pneumococcal phage Cp-1 lysin (Cpl-1) and staphylococcal phage 187 lysin (Ply187) indicated that PlyGBS has three different domains. The N-terminal 107 amino acids are 27% identical to a domain in Ply187 that functions as an endopeptidase. For amino acids 150-394 (central domain), PlyGBS displays 46% identity to the N-terminal muramidase domain of Cpl-1. Two acidic amino acids, Asp and Glu, are also present in PlyGBS at positions 158 (Asp) and 185 (Glu).

Example 2

Characterization of PlyGBS

Based on the deduced amino acid sequence, PlyGBS has a theoretical pI value (isoelectric point) of 4.88. With 25 mM Tris-HCl (pH 7.4) as elution buffer in ion-exchange chromatography, the protein was negatively charged and bound to a positively charged Q-Sepharose anion exchanger. The enzyme was eluted by an NaCl gradient and the active fractions were pooled and analyzed by SDS-PAGE. The major protein band at about 50 KDa correlated with the calculated molecular mass for PlyGBS (49.6 KDa). The final preparation, estimated to be >95% pure by scanning densitometry on the Coomassie-stained SDS-PAGE gel, was used for all subsequent experiments.

The pH optimum of purified PlyGBS was determined to be around 5.0 with an active pH range between 4.0.0. Gel filtration chromatography of PlyGBS indicates that the protein functions as a monomer.

Example 3

PlyGBS Activity In Vitro

Optical Density In Vitro Lytic Killing Assay

To test the in vitro PlyGBS activity on various bacterial strains, all strains were inoculated overnight, subcultured (1:100), and grown to $OD_{600}$=0.3. Cells were centrifuged and resuspended in ⅒ volume of phosphate buffer (40 mM, pH 5.0). 100 microliter aliquots of the bacteria solution ($5 \times 10^8$-$10^9$ cfu/ml) were incubated with indicated amounts of PlyGBS at 37 degrees C. for 60 min. A spectrophotometer was used to monitor the lytic activity, measured as the drop in milli$OD_{600}$ per minute ($-mOD_{600}$/min). The initial velocity of this reaction is defined as the rate of lysis. To determine bacteria viability, cells of GBS strain NCTC11237 from the above assay were centrifuged, diluted and plated on THY agar plates for cell counts. All experiments were performed in triplicates and control experiments with the addition of phosphate buffer (pH 5.0) were performed under the same conditions.

To determine the PlyGBS activity in vitro against GBS cells, GBS cells (NCTC 11237, serotype IIIR) were mixed with 40 units of PlyGBS at 37 degrees C. for 60 min. The $OD_{600}$ dropped to baseline within 10 min indicating a rapid rate of cell lysis, which is corroborated by the 2 log decrease in viability observed at 60 minutes. When multiple strains of GBS, representing serotypes Ia, Ib, Ic/II, IIR, IIIR as well as the predominant serotypes III, and V, were tested for PlyGBS sensitivity based on lytic activity, a similar velocity of lysis ($-mOD_{600}$/min) was observed with certain strain-to-strain variation.

In addition to GBS, bacterial strains representing a variety of species were analyzed to determine their sensitivity to PlyGBS in vitro. Of the tested streptococcal strains belonging to different Lancefield groups, PlyGBS had significant lytic activity against groups A, C, G and L streptococci, with little to no activity against groups D, E and N. The muralytic activity of the PlyGBS was also tested against non-Lancefield oral streptococcal species including *S. gordonii, S. oralis, S. salivarius, S. sobrinus,* and *S. mutans*. PlyGBS had medium to low activity against *S. salivarius, S. gordonii* and *S. mutans*, but no activity against the other two commensal species tested. No lytic activity was observed with two non-streptococcal gram-positive species, *Bacillus cereus* and *Staphylococcus aureus*, or two vaginal commensal bacteria, *Lactobacillus acidophilus* and *L. crispatus*.

Phase contrast and electron microscopy were used to visualize the lytic effect of lysin on GBS cells (an example of "lytic activity"). Normally, intact GBS form short chains in a buffer control. After treatment with PlyGBS lysin, the cells were lysed, releasing the cytoplasmic contents and becoming opaque by light microscopy. As seen with other lysins by electron microscopy, a weakness in the cell wall produced by PlyGBS results in extrusions and rupture of the cytoplasmic membrane, which appears to be more localized within the septum region of the dividing cells. Subsequent loss of cytoplasmic contents transforms the cells into empty "cell ghosts".

Example 4

PlyGBS Activity In Vivo

Mouse Model In Vivo Killing Assay

Six-week-old BALB/c female mice were purchased from Charles River Laboratories (Wilmington, Mass.). Because bacterial colonization in the mouse vaginal cavity is believed to be more efficient at estrus, the estral cycle of all mice was synchronized on day 1 by subcutaneous inoculation of 0.1 mg of β-estradiol valerate. On day 3, thirty mice were anesthetized and inoculated vaginally with ~$10^6$ streptomycin resistant GBS NCTC11237 cells using a micropipette (20 μl dose in 40 mM phosphate buffer, pH 5.0). On day 4, mice were treated vaginally with 20 μl phosphate buffer (pH 5.0) and swabbed with calcium alginate fiber tipped ultrafine swabs (Fischer, Pittsburgh, Pa.). The surfaces of THY agar plates containing 5% sheep blood and streptomycin (200 μg/ml) were streaked with the wet swabs to determine baseline colonization. Mice were then randomized to be treated vaginally with either 20 μl phosphate buffer, pH 5.0 (n=15) or 10 units of PlyGBS lysin (n=15). At 2 and 4 hrs post-treatment, all mice were swabbed again for titer determination.

To test if PlyGBS can be used for postpartum treatment of newborns, 38 mice received an upper respiratory challenge of about 108 StrR GBS NCTC11237 cells (20 µl orally and 20 µl to each nostril). The next morning, mice were oropharyngeally swabbed and baseline colonization was enumerated as described above. Mice were randomized and administrated orally and nasally with either 20 µl phosphate buffer, pH 5.0 (n=18) or 10 Units PlyGBS lysin (n=20). At 2 and 24 hrs post-treatment, all mice were oropharyngeally swabbed to determine the bacterial count.

For statistical analysis, MIXED Model (from SAS Mixed Procedure) was used to compare the colonization status between groups. A P value <0.05 was considered significant.

An in vivo killing assay was performed to assess the in vivo lytic activity of PlyGBS was tested by administering PlyGBS to colonized GBS in a mouse vagina model. To perform this test, two groups of mice were challenged vaginally with $10^6$ cfu StrR GBS cells. Subsequently, 24 hours later, the vaginal cavities were swabbed to determine the initial colonization rate (0 hr samples, pre-treatment). The mice were then treated vaginally with either buffer (n=15) or PlyGBS (n=15) and swabbed 2 hrs and 4 hrs post-treatment. Negligible effect was observed in the buffer control animals. In contrast, animals treated with a single dose of PlyGBS showed a significant reduction (approximately 3 log drop) in the bacterial load at both the 2 hr and 4 hr intervals when compared to buffer control (p<0.0001).

Similarly, two groups of mice were challenged with a total of $10^8$ cfu StrR GBS delivered orally and nasally to determine if PlyGBS can be used to reduce colonized GBS in the mouse upper respiratory tract. Mice treated with a single dose of lysin by the same route exhibited a significant reduction in GBS colonization at both the 2 hr and 24 hr swabbing intervals when compared to the buffer control group (p<0.0001).

Example 5

PlyGBS Mutant Lysin Production by Mutagenesis Using an *E. coli* Mutator Strain

*Escherichia coli* XL-1 Red strain (Stratagene, Inc., La Jolla, Calif., Table 3) was used to generate random mutations in PlyGBS due to deficiency in three primary DNA repair pathways (muts, mutD, and mutT) that result in a significantly higher mutation rate than the wild-type strain. Plasmid pCQJ67-2 containing the wild type plyGBS gene was transformed into *E. coli* XL-1 Red and propagated on LB plates supplemented with kanamycin (50 µg/ml) 37 degrees C. overnight. Colonies were scraped from the agar plates and subcultured (1:100) for another overnight growth, allowing mutations to accumulate in the plasmid DNA. The next morning, the culture was subcultured to grow for an extra 6 hr and plasmid DNA was prepared. The resultant plasmids containing random mutations were transformed into the protein expression strain *E. coli* BL21(DE3) and over 5,000 clones were screened for lysin activity better than wild type PlyGBS, using the clear zone method as previously described in Schuch, R., D. Nelson, and V. A. Fischetti, "A bacteriolytic agent that detects and kills *Bacillus anthracis*," Nature 418: 884-889 (2002). To avoid any potential mutations in promoter region, plasmid DNA from clones with better than wild type activity was prepared and digested with NcoI and XhoI. The released plyGBS gene fragment was cloned into pET28a and the resultant plasmid was transform into *E. coli* BL21 (DE3) to confirm the increased lysin activity. DNA sequence analysis was used to locate the mutations.

Example 6

Gene Mutagenesis Using Error-Prone PCR Method

Another mutagenesis method utilized was the "Diversify PCR Random Mutagenesis Kit" (BD Bioscience, Palo Alto, Calif.). The procedure involves performing a PCR reaction under conditions that reduce the fidelity of nucleotide incorporation, cloning the resulting PCR fragments, and then screening the library for novel mutations with improved lysin activity. The PCR mutation rate was chosen around 2.7 per 1,000 bp by keeping the manganese concentration at 320 µM in the reaction. Two PCR primers are listed in Cheng, Q. et al., "Removal of group B streptococci colonizing the vagina and oropharynx of mice with a bacteriophage lytic enzyme," Antimicrob. Agents Chemother. 49: 111-117 (2005). The PCR product was digested with NcoI and XhoI, and cloned into pET28a for screening, using the method mentioned above. Multiple rounds of PCR mutagenesis were performed to improve the lysin activity.

Example 7

Construction of plyGBS Deletion Mutants

Several deletion mutants were constructed based on the domain organization of wild-type plyGBS and a schematic map is shown in FIG. 4. All the regions were PCR-amplified and cloned into pET28a for protein expression. Mutant PlyGBS92 (SEQ ID NO:6), expressed from the plasmid pCQJ92 (Table 3), encodes the putative muramidase domain [amino acid (aa) 150-394]. Mutant PlyGBS93 (SEQ ID NO:7) contains the region of aa 150-443, which deletes the N-terminal endopeptidase domain. Mutant PlyGBS94 (SEQ ID NO:8), expressed from pCQJ94 (Table 3), contains the first 146 aa that is the putative endopeptidase domain. Another mutant, PlyGBS95 (SEQ ID NO:9), containing a deletion of the central muramidase domain (deletion between aa 147-348), was expressed from pCQJ95 constructed by inserting the HindIII/XhoI digested PCR fragment (C-terminus of plyGBS gene, bp 1045-1332) into pCQJ94. All the constructed plasmids for mutant expression were sequenced to confirm the expected deletion.

Example 8

Comparison of Lysin Activity and Stability

To compare the lysin activity of various mutants, clones were grown and induced for protein over-expression in 10 ml volumes under the same condition described in Cheng, Q. et al., "Removal of group B streptococci colonizing the vagina and oropharynx of mice with a bacteriophage lytic enzyme," Antimicrob. Agents Chemother. 49: 111-117 (2005). Protein crude extracts were used for the in vitro activity assay. In order to quantitate the protein activity, large batch (1 liter) cultures were made of each mutant. Because the mutants had a similar pI (Isoelectric point) to the wild-type enzyme (Table 1), purification was achieved by anion exchange chromatography as described Cheng, Q. et al., "Removal of group B streptococci colonizing the vagina and oropharynx of mice with a bacteriophage lytic enzyme," Antimicrob. Agents Chemother. 49: 111-117 (2005). Active fractions were pooled and electrophoresed on a 4-20% gradient Tris-HCl pre-cast SDS-PAGE gel (Bio-Rad, Hercules, Calif.). Lysin activity was quantitated as described in Cheng, Q. et al., "Removal of group B streptococci colonizing the vagina and oropharynx of mice with a bacteriophage lytic enzyme," Antimicrob. Agents Chemother. 49: 111-117 (2005). Protein concentration was determined using BCA Protein Assay Kit (Pierce, Rockford, Ill.) to calculate the specific activity for each mutant.

Because the PlyGBS90-1 (SEQ ID NO:5) and PlyGBS90-8 (SEQ ID NO:4) mutants obtained from random mutagenesis had a specific activity significantly higher than wild-type PlyGBS, the stability of the mutants was compared with wild-type under storage conditions. Fresh-purified wild-type PlyGBS, as well as two mutants PlyGBS90-1 (SEQ ID NO:5) and PlyGBS90-8 (SEQ ID NO:4), were stored directly at 4 degrees C. or in 25% glycerol at −80 degrees C. An in vitro activity assay was performed at different time points (0, 20, 40, and 60 days) using a spectrophotometer to monitor the lytic activity, measured as the drop in milliOD600 per minute (−mOD600/min). The in vitro activity assay was performed as described in Cheng, Q. et al., "Removal of group B streptococci colonizing the vagina and oropharynx of mice with a bacteriophage lytic enzyme," Antimicrob. Agents Chemother. 49: 111-117 (2005). The initial velocity of this reaction (Vmax) is defined as the rate of lysis and was used to compare protein stability at various time intervals.

Example 9

Characteristics of Hyperactive Mutant PlyGBS90-1 (SEQ ID NO:5)

Characteristics of the hyperactive mutant PlyGBS90-1 (SEQ ID NO:5) were compared to compared to wild-type PlyGBS. The in vitro lytic activity of PlyGBS90-1 (SEQ ID NO:5) was measured by two different methods. First, we used various amount of purified PlyGBS90-1 (SEQ ID NO:5) and wild type PlyGBS (2, 10, 50, and 100 μg) in the in vitro assay to measure the Vmax value, as described in Cheng, Q. et al., "Removal of group B streptococci colonizing the vagina and oropharynx of mice with a bacteriophage lytic enzyme," Antimicrob. Agents Chemother. 49: 111-117 (2005). We also tested the killing efficacy of mutant PlyGBS90-1 (SEQ ID NO:5) on GBS in an in vitro viability assay, as described in Cheng, Q. et al., "Removal of group B streptococci colonizing the vagina and oropharynx of mice with a bacteriophage lytic enzyme," Antimicrob. Agents Chemother. 49: 111-117 (2005). The specificity and the optimum pH of the mutant were analyzed as described in Cheng, Q. et al., "Removal of group B streptococci colonizing the vagina and oropharynx of mice with a bacteriophage lytic enzyme," Antimicrob. Agents Chemother. 49: 111-117 (2005).

To test the effect of salt concentration on lytic activity, purified PlyGBS90-1 (SEQ ID NO:5) and PlyGBS were dialyzed against 2 mM Tris-HCl (pH 7.4) overnight. Various amount of 5M NaCl was added into the dialyzed protein samples to determine the Vmax values under 0-500 mM salt concentration using a spectrophotometer, as described in Cheng, Q. et al., "Removal of group B streptococci colonizing the vagina and oropharynx of mice with a bacteriophage lytic enzyme," Antimicrob. Agents Chemother. 49: 111-117 (2005).

Example 10

In Vivo Activity of the Mutant PlyGBS90-1 (SEQ ID NO:5)

The mutant PlyGBS90-1 (SEQ ID NO:5) was tested in vivo against GBS in a mouse vaginal model developed in a previous study (Cheng, Q., D. Nelson, S. W. Zhu, and V. A. Fischetti, "Removal of group B streptococci colonizing the vagina and oropharynx of mice with a bacteriophage lytic enzyme," Antimicrob. Agents Chemother. 49: 111-117 (2005), incorporated herein by reference). Briefly, on day 1, the estral cycle of 20 six-week-old BALB/c female mice (Charles River Lab, Wilmington, Mass.) were synchronized by β-estradiol valerate (McLean, N. W, and I. J. Rosenstein, "Characterization and selection of a Lactobacillus species to recolonize the vagina of women with recurrent bacterial vaginosis," J. Med. Microbiol. 49: 543-552 (2000)). On day 3, the mice were challenged vaginally with 106 colony forming unit (cfu) StRR NCTC11237 GBS cells. On day 4, the vaginal cavities were swabbed to determine the colonization status pre-treatment (0 hr samples). The mice were then randomized into three groups and treated vaginally with either buffer (n=10), 1,500 μg of PlyGBS (n=10), or 1,500 μg of mutant PlyGBS90-1 (SEQ ID NO:5) (n=10). Mice were then swabbed vaginally 2 hrs and 4 hrs post-treatment. THY agar plates (Nelson, D., L. Loomis, and V. A. Fischetti, "Prevention and elimination of upper respiratory colonization of mice by group A streptococci by using a bacteriophage lytic enzyme," Proc. Natl. Acad. Sci. USA 98: 4107-4112 (2001), incorporated herein by reference), supplemented with 5% sheep blood and streptomycin (200 μg/ml), were used to determine the colony counts from wet swabs. MIXED Model (from SAS Mixed Procedure) was used to compare the colonization status between groups in statistical analysis and a P value <0.05 was considered significant.

TABLE 3

BACTERIA STRAINS AND PLASMIDS

| BACTERIA | Strain | Seortype | Source[a] |
|---|---|---|---|
| GBS | NCTC11237 | IIIR | 1 |
|  | NCTC11237 derivative | IIIR, Str[R] | 2 |
| ESCHERICHIA COLI | XL-1 Red | | 3 |
|  | BL21(DE3) | | 2 |
| STREPTOCOCCUS SALIVARIUS | ATCC9222 | | 4 |
| BACILLUS CEREUS | ATCC4342 | | 2 |
| STAPHYLOCOCCUS AUREUS | RN6390 | | 2 |

| LASMIDS | Phenotype | Encoded protein | DESCRIPTION |
|---|---|---|---|
| CQJ67-2 CQJ67-2 DERIVATIVE | Kan[R] | Wt PlyGBS | Wt plyGBS gene cloned into pET28a ( ) |
| PCQJ86-6 | Kan[R] | PlyGBS86-6 | A point mutation in plyGBS gene caused D374E change |

TABLE 3-continued

| | | BACTERIA STRAINS AND PLASMIDS | |
|---|---|---|---|
| PCQJ80 | Kan^R | PlyGBS80 | A mutant contains the first 163 amino acids of PlyGBS due to a nonsense mutation. |
| PCQJ90-1 | Kan^R | PlyGBS90-1 | A mutation has an out-of-frame deletion in plyGBS gene (bp 424-1255). It expresses the first 141 amino acids of PlyGBS plus extra 13 amino acids due to the frameshift. |
| PCQJ90-8 | Kan^R | PlyGBS90-8 | A mutant contains the first 138 amino acids of PlyGBS due to a nonsense mutation. |
| LYGBS DELETION UTANTS | | | |
| PCQJ92 | Kan^R | PlyGBS92 | 738 bp PCR fragment cloned into pET28a by NcoI/XhoI. The resultant plasmid encodes the muramidase domain (amino acid 150-394) of the PlyGBS |
| PCQJ93 | Kan^R | PlyGBS93 | 885 bp PCR fragment cloned into pET28a by NcoI/XhoI. The resultant plasmid encodes the muramidase domain plus C-terminal region (amino acid 150-443) of PlyGBS. |
| PCQJ94 | Kan^R | PlyGBS94 | 441 bp PCR fragment cloned into pET28a by NcoI/HindIII. pCQJ94 encodes the N-terminal endopeptidase domain (amino acid 1-146) of the PlyGBS. |
| PCQJ95 | Kan^R | PlyGBS95 | 288 bp PCR fragment (C-terminus of plyGBS gene, bp 1045-1332) cloned into pCQJ94 by HindIII/XhoI. The resultant plasmid encodes a PlyGBS mutant which has a deletion in central muramidase domain (deletion between amino acid 147-348). |

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A composition comprising a hyperactive PlyGBS mutant lysin having greater killing activity against Group B Streptococcus (GBS) cells compared with the PlyGBS protein, the PlyGBS mutant lysin of the amino acid sequence selected from the group consisting of: PlyGBS 90-1 (SEQ ID NO: 5), PlyGBS 95 (SEQ ID NO: 9), PlyGBS 86-6 (SEQ ID NO: 2), PlyGBS 80 (SEQ ID NO: 3), PlyGBS 90-8 (SEQ ID NO: 4) and PlyGBS 94 (SEQ ID NO: 8).

2. A composition comprising a hyperactive PlyGBS mutant lysin having greater killing activity against Group B Streptococci (GBS) cells compared with the PlyGBS protein, the PlyGBS mutant lysin consisting of the amino acid sequence of SEQ ID NO: 1 with a modification selected from the group consisting of:
   a. the PlyGBS mutant is a mutant lysin containing only one catalytic domain selected from the group consisting of the endopeptidase domain and the muramidase domain;
   b. the PlyGBS mutant is a truncated mutant lysin without the C-terminal domain; and
   c. the PlyGBS mutant having the substitution of glutamic acid for the aspartic acid residue at position 374 of SEQ ID NO: 1.

3. The composition of claim 2, where the PlyGBS mutant lysin comprises the endopeptidase domain of SEQ ID NO: 1 without a C-terminal domain.

4. The composition of claim 3, where the PlyGBS mutant lysin comprises amino acid residues 1-107 of SEQ ID NO: 1.

5. The composition of claim 2, where the PlyGBS mutant lysin does not include the muramidase domain of amino acid residues 147-348 of SEQ ID NO: 1.

6. The composition of claim 2, where the PlyGBS mutant lysin is selected from the group consisting of: PlyGBS 86-6 (SEQ ID NO: 2), PlyGBS 80 (SEQ ID NO: 3), PlyGBS 90-8 (SEQ ID NO: 4), PlyGBS 90-1 (SEQ ID NO: 5), PlyGBS 94 (SEQ ID NO: 8), and PlyGBS 95 (SEQ ID NO: 9).

7. The composition of claim 2, where the PlyGBS mutant lysin is selected from the group consisting of: PlyGBS 80 (SEQ ID NO: 3), PlyGBS 90-8 (SEQ ID NO: 4), PlyGBS 90-1 (SEQ ID NO: 5), PlyGBS 94 (SEQ ID NO: 8), and PlyGBS 95 (SEQ ID NO: 9).

8. The composition of claim 2, where the PlyGBS mutant lysin is PlyGBS 90-1 (SEQ ID NO: 5).

9. The composition of claim 2, further comprising a pharmaceutically acceptable carrier, stabilizing buffer, or mucoadhesive.

10. A method of treating an infection or bacterial colonization comprising the step of administering to a subject a composition comprising an isolated polypeptide comprising a hyperactive PlyGBS mutant lysin having greater killing activity against Group B Streptococci (GBS) bacteria compared with the PlyGBS protein; the mutant lysin consisting of the amino acid sequence of SEQ ID NO: 1 with a modification selected from the group consisting of:
   a. the PlyGBS mutant is a mutant lysin containing only one catalytic domain selected from the group consisting of the an endopeptidase domain and the muramidase domain;
   b. the PlyGBS mutant is a truncated mutant lysin without the C-terminal domain; and
   c. the PlyGBS mutant having the substitution of glutamic acid for the aspartic acid residue at position 374 of SEQ ID NO: 1.

11. The method of claim 10, where the PlyGBS mutant lysin comprises amino acid residues 1-107 of SEQ ID NO: 1.

12. The method of claim 10, where the PlyGBS mutant lysin does not include the muramidase domain of amino acid residues 147-348 of SEQ ID NO: 1.

13. The method of claim 10, where the PlyGBS mutant lysin comprises amino acid residues 1-138 of SEQ ID NO: 1.

14. The method of claim 10, where the mutant lysin is a polypeptide selected from the group consisting of: PlyGBS 86-6 (SEQ ID NO: 2), PlyGBS 80 (SEQ ID NO: 3), PlyGBS 90-8 (SEQ ID NO: 4), PlyGBS 90-1 (SEQ ID NO: 5), PlyGBS 94 (SEQ ID NO: 8), and PlyGBS 95 (SEQ ID NO: 9).

15. The method of claim 10, where the PlyGBS mutant lysin is selected from the group consisting of: PlyGBS 80 (SEQ ID NO: 3), PlyGBS 90-8 (SEQ ID NO: 4), PlyGBS 90-1 (SEQ ID NO: 5), PlyGBS 94 (SEQ ID NO: 8), and PlyGBS 95 (SEQ ID NO: 9).

16. The method of claim 15, where the composition is characterized by one or more of the following: a pH of about 5.0, a NaCl at a concentration of about 50-100 mM and comprises about 10 to 100 enzyme units of the PlyGBS mutant per mL of the composition.

17. The method of claim 10, where the composition has a pH of about 5.0.

18. The method of claim 10, where the composition comprises NaCl at a concentration of about 50-100 mM.

* * * * *